US011136358B2

(12) United States Patent
Kim et al.

(10) Patent No.: US 11,136,358 B2
(45) Date of Patent: Oct. 5, 2021

(54) PLASMID-BASED CTX PHAGE REPLICATION SYSTEM AND VIBRIO CHOLERAE STRAIN THAT CAN BE INFECTED BY CTX PHAGE AND CAN BE USED FOR CHOLERA TOXIN PRODUCTION

(71) Applicant: INDUSTRY-UNIVERSITY COOPERATION FOUNDATION HANYANG UNIVERSITY ERICA CAMPUS, Ansan-si (KR)

(72) Inventors: Dong Wook Kim, Seoul (KR); Eun Jin Kim, Seoul (KR); Hyun Jin Yu, Incheon (KR)

(73) Assignee: INDUSTRY-UNIVERSITY COOPERATION FOUNDATION HANYANG UNIVERSITY ERICA CAMPUS, Ansari-si (KR)

( * ) Notice: Subject to any disclaimer, the term of this patent is extended or adjusted under 35 U.S.C. 154(b) by 0 days.

(21) Appl. No.: 16/442,164

(22) Filed: Jun. 14, 2019

(65) Prior Publication Data

US 2019/0315813 A1 Oct. 17, 2019

Related U.S. Application Data

(63) Continuation of application No. PCT/KR2017/014782, filed on Dec. 15, 2017.

(30) Foreign Application Priority Data

Dec. 16, 2016 (KR) ........................ 10-2016-0172681
Dec. 16, 2016 (KR) ........................ 10-2016-0172684
Nov. 1, 2017 (KR) ........................ 10-2017-0144851

(51) Int. Cl.

| | |
|---|---|
| ***A61K 39/00*** | (2006.01) |
| ***A61K 39/02*** | (2006.01) |
| ***A61K 39/106*** | (2006.01) |
| ***C07K 14/28*** | (2006.01) |
| ***C12N 15/74*** | (2006.01) |
| ***C12N 7/00*** | (2006.01) |
| ***C12N 15/65*** | (2006.01) |
| ***C12P 21/02*** | (2006.01) |
| ***C12N 1/20*** | (2006.01) |
| *C12R 1/63* | (2006.01) |

(52) U.S. Cl.

CPC .............. *C07K 14/28* (2013.01); *C12N 1/205* (2021.05); *C12N 7/00* (2013.01); *C12N 15/65* (2013.01); *C12N 15/74* (2013.01); *C12P 21/02* (2013.01); *C12N 2795/00042* (2013.01); *C12R 2001/63* (2021.05)

(58) Field of Classification Search

CPC .......................... A61K 39/02; A61K 2039/106
USPC .......... 424/184.1, 185.1, 190.1, 234.1, 261.1
See application file for complete search history.

(56) References Cited

U.S. PATENT DOCUMENTS

| | | | |
|---|---|---|---|
| 5,631,010 | A | 5/1997 | Mekalanos |
| 2008/0305125 | A1 | 12/2008 | Hirst |

OTHER PUBLICATIONS

International Search Report issued in PCT/KR2017/014782; dated Dec. 10, 2018.
Office Action issued in KR 10-2016-0172681; mailed by the Korean Intellectual Property Office dated Dec. 16, 2017.
Brigid M Davis et al.; "Filamentous Phages Linked to Virulence of Vibrio cholerae"; Current Opinion in Microbiology; 2003; pp. 35-42; vol. 6.
Eun Jin Kim; "A Study on the Evolution of Atypical Vibrio cholerae O1 El Tor Variants"; Doctoral Thesis, Department of Pharmacy, The Graduate School of Hanyang University; Aug. 2015; pp. 1-116.
NCBI, GenBank Accession No. KF664568.1; Sep. 24, 2014; pp. 1-5.
NCBI, GenBank Accession No. CAA45465.1; Jul. 26, 2016; p. 1.
Eun Jin Kim et al.; "Replication of Vibrio cholerae Classical CTX Phage"; Proceedings of the National Academy of Sciences of the United States of America; Feb. 28, 2017; pp. 2343-2348; vol. 114, No. 9.
NCBI, GenBank Accession No. KJ782405.1; Sep. 3, 2015; pp. 1-2.

*Primary Examiner* — Rodney P Swartz
(74) *Attorney, Agent, or Firm* — Studebaker & Brackett PC

(57) ABSTRACT

The present invention relates to a plasmid-based CTX phage replication system and *Vibrio cholerae* strain that can be infected by CTX phage and can be used for cholera toxin production. More particularly, the present invention provides a *Vibrio cholera* variant strain, which expresses a toxT protein in which tyrosine at position 139 is substituted by phenylalanine through the point mutation of a toxT gene using a plasmid-based CTX phage replication system, and is used as a receptor strain which can improve CTX phage infection efficiency and allows a plurality of CTX prophages to simultaneously infect the strain and to be inserted into the chromosome thereof, which the consequent provision of the effect of increasing the production yield of a cholera toxin.

5 Claims, 9 Drawing Sheets

Specification includes a Sequence Listing.

SEQUENCE LISTING

<160> NUMBER OF SEQ ID NOS: 17

<210> SEQ ID NO 1
<211> LENGTH: 777
<212> TYPE: DNA
<213> ORGANISM: Artificial Sequence
<220> FEATURE:
<223> OTHER INFORMATION: ctxA

<400> SEQUENCE: 1

```
atggtaaaga taatatttgt gtttttattt ttcttatcat cattttcata tgcaaatgat     60

gataagttat atcgggcaga ttctagacct cctgatgaaa taaagcagtc aggtggtctt    120

atgccaagag gacagagtga gtactttgac cgaggtactc aaatgaatat caacctttat    180

gatcatgcaa gaggaactca gacgggattt gttaggcacg atgatggata tgtttccacc    240

tcaattagtt tgagaagtgc ccacttagtg ggtcaaacta tattgtctgg tcattctact    300

tattatatat atgttatagc cactgcaccc aacatgttta acgttaatga tgtattaggg    360

gcatacagtc ctcatccaga tgaacaagaa gtttctgctt taggtgggat tccatactcc    420

caaatatatg gatggtatcg agttcatttt ggggtgcttg atgaacaatt acatcgtaat    480

aggggctaca gagatagata ttacagtaac ttagatattg ctccagcagc agatggttat    540

ggattggcag gtttccctcc ggagcataga gcttggaggg aagagccgtg gattcatcat    600

gcaccgccgg gttgtgggaa tgctccaaga tcatcgatga gtaatacttg cgatgaaaaa    660

acccaaagtc taggtgtaaa attccttgac gaataccaat ctaaagttaa aagacaaata    720

ttttcaggct atcaatctga tattgataca cataatagaa ttaaggatga attatga       777
```

<210> SEQ ID NO 2
<211> LENGTH: 375
<212> TYPE: DNA
<213> ORGANISM: Artificial Sequence
<220> FEATURE:
<223> OTHER INFORMATION: ctxB

<400> SEQUENCE: 2

```
atgattaaat taaaatttgg tgtttttttt acagttttac tatcttcagc atatgcacat     60

ggaacacctc aaaatattac tgatttgtgt gcagaatacc acaacacaca aatatatacg    120

ctaaatgata agatattttc gtatacagaa tctctagctg gaaaaagaga gatggctatc    180

attactttta agaatggtgc aatttttcaa gtagaagtac caggtagtca acatatagat    240

tcacaaaaaa aagcgattga aaggatgaag gataccctga ggattgcata tcttactgaa    300

gctaaagtcg aaaagttatg tgtatggaat aataaaacgc ctcatgcgat tgccgcaatt    360

agtatggcaa attaa                                                     375
```

<210> SEQ ID NO 3
<211> LENGTH: 166
<212> TYPE: DNA
<213> ORGANISM: Artificial Sequence
<220> FEATURE:
<223> OTHER INFORMATION: ctxB fragment

<400> SEQUENCE: 3

```
atgattaaat taaaatttgg tgtttttttt acagttttac tatcttcagc atatgcacat     60
```

```
ggaacacctc aaaatattac tgatttgtgt gcagaatacc acaacacaca aatatatacg    120

ctaaatgata agatattttc gtatacagaa tctctagctg gaaaaa                    166


<210> SEQ ID NO 4
<211> LENGTH: 816
<212> TYPE: DNA
<213> ORGANISM: Artificial Sequence
<220> FEATURE:
<223> OTHER INFORMATION: kanamycin gene

<400> SEQUENCE: 4

atgagccata ttcaacggga aacgtcttgc tctaggccgc gattaaattc caacatggat     60

gctgatttat atgggtataa atgggctcgc gataatgtcg ggcaatcagg tgcgacaatc    120

tatcgattgt atgggaagcc cgatgcgcca gagttgtttc tgaaacatgg caaaggtagc    180

gttgccaatg atgttacaga tgagatggtc agactaaact ggctgacgga atttatgcct    240

cttccgacca tcaagcattt tatccgtact cctgatgatg catggttact caccactgcg    300

atccccggga aaacagcatt ccaggtatta gaagaatatc ctgattcagg tgaaaatatt    360

gttgatgcgc tggcagtgtt cctgcgccgg ttgcattcga ttcctgtttg taattgtcct    420

tttaacagcg atcgcgtatt tcgtctcgct caggcgcaat cacgaatgaa taacggtttg    480

gttgatgcga gtgattttga tgacgagcgt aatggctggc ctgttgaaca agtctggaaa    540

gaaatgcata aacttttgcc attctcaccg gattcagtcg tcactcatgg tgatttctca    600

cttgataacc ttatttttga cgaggggaaa ttaataggtt gtattgatgt tggacgagtc    660

ggaatcgcag accgatacca ggatcttgcc atcctatgga actgcctcgg tgagttttct    720

ccttcattac agaaacggct ttttcaaaaa tatggtattg ataatcctga tatgaataaa    780

ttgcagtttc atttgatgct cgatgagttt ttctaa                              816


<210> SEQ ID NO 5
<211> LENGTH: 1542
<212> TYPE: DNA
<213> ORGANISM: Artificial Sequence
<220> FEATURE:
<223> OTHER INFORMATION: CTX prophage genome substituted ctxA and ctxB
      fragment with kanamycin resistant gene
<220> FEATURE:
<221> NAME/KEY: gene
<222> LOCATION: (420)..(1251)
<223> OTHER INFORMATION: kanamycin resistant gene
<220> FEATURE:
<221> NAME/KEY: gene
<222> LOCATION: (1264)..(1472)
<223> OTHER INFORMATION: ctxB

<400> SEQUENCE: 5

tgcatcgagc taccgctaca aggtgctacc gttaccggat ttcaatcact ttgtggtgtt     60

cgataccttt gcagcgcaag cgctgtgggt agaagtgaaa cggggtttac cgataaaaac    120

agaaaatgat aaaaaaggac taaatagtat attttgattt ttgatttttg acttttgatt    180

tcaaataata caaatttatt tacttattta attgttttga tcaattattt ttctgttaaa    240

caaagggagc attatcgggg atccccggca gattacgcgc agaaaaaaag gatctcaaga    300

agatcctttg atcttttcta cggggtctga cgctcagtgg aacgaaaact cacgttaagg    360

gattttggtc atgaacaata aaactgtctg cttacataaa cagtaataca aggggtgtta    420

tgagccatat tcaacgggaa acgtcttgct ctaggccgcg attaaattcc aacatggatg    480

ctgatttata tgggtataaa tgggctcgcg ataatgtcgg gcaatcaggt gcgacaatct    540
```

-continued atcgattgta tgggaagccc gatgcgccag agttgtttct gaaacatggc aaaggtagcg 600
ttgccaatga tgttacagat gagatggtca gactaaactg gctgacggaa tttatgcctc 660
ttccgaccat caagcatttt atccgtactc ctgatgatgc atggttactc accactgcga 720
tccccgggaa aacagcattc caggtattag aagaatatcc tgattcaggt gaaaatattg 780
ttgatgcgct ggcagtgttc ctgcgccggt tgcattcgat tcctgtttgt aattgtcctt 840
ttaacagcga tcgcgtattt cgtctcgctc aggcgcaatc acgaatgaat aacggtttgg 900
ttgatgcgag tgattttgat gacgagcgta atggctggcc tgttgaacaa gtctggaaag 960
aaatgcataa acttttgcca ttctcaccgg attcagtcgt cactcatggt gatttctcac 1020
ttgataacct tatttttgac gaggggaaat taataggttg tattgatgtt ggacgagtcg 1080
gaatcgcaga ccgataccag gatcttgcca tcctatggaa ctgcctcggt gagttttctc 1140
cttcattaca gaaacggctt tttcaaaaat atggtattga taatcctgat atgaataaat 1200
tgcagtttca tttgatgctc gatgagtttt tctaagccct gcagggcgag agatggctat 1260
cattactttt aagaatggtg caatttttca agtagaagta ccaggtagtc aacatataga 1320
ttcacaaaaa aaagcgattg aaaggatgaa ggatatcctg aggattgcat atcttactga 1380
agctaaagtc gaaaagttat gtgtatggaa taataaaacg cctcatgcga ttgccgcaat 1440
tagtatggca aattaagata taaaaaagcc cacctcagtg ggcttttttg tggttcgatg 1500
atgagaagca accgttttgc ccaaacatgt attactgcaa gt 1542

<210> SEQ ID NO 6
<211> LENGTH: 276
<212> TYPE: PRT
<213> ORGANISM: Vibrio cholerae

<400> SEQUENCE: 6

```
Met Ile Gly Lys Lys Ser Phe Gln Thr Asn Val Tyr Arg Met Ser Lys
1               5                   10                  15

Phe Asp Thr Tyr Ile Phe Asn Asn Leu Tyr Ile Asn Asp Tyr Lys Met
            20                  25                  30

Phe Trp Ile Asp Ser Gly Ile Ala Lys Leu Ile Asp Lys Asn Cys Leu
        35                  40                  45

Val Ser Tyr Glu Ile Asn Ser Ser Ser Ile Ile Leu Leu Lys Lys Asn
    50                  55                  60

Ser Ile Gln Arg Phe Ser Leu Thr Ser Leu Ser Asp Glu Asn Ile Asn
65                  70                  75                  80

Val Ser Val Ile Thr Ile Ser Asp Ser Phe Ile Arg Ser Leu Lys Ser
                85                  90                  95

Tyr Ile Leu Gly Asp Leu Met Ile Arg Asn Leu Tyr Ser Glu Asn Lys
            100                 105                 110

Asp Leu Leu Leu Trp Asn Cys Glu His Asn Asp Ile Ala Val Leu Ser
        115                 120                 125

Glu Val Val Asn Gly Phe Arg Glu Ile Asn Tyr Ser Asp Glu Phe Leu
    130                 135                 140

Lys Val Phe Phe Ser Gly Phe Phe Ser Lys Val Glu Lys Lys Tyr Asn
145                 150                 155                 160

Ser Ile Phe Ile Thr Asp Asp Leu Asp Ala Met Glu Lys Ile Ser Cys
                165                 170                 175

Leu Val Lys Ser Asp Ile Thr Arg Asn Trp Arg Trp Ala Asp Ile Cys
            180                 185                 190
```

-continued

```
Gly Glu Leu Arg Thr Asn Arg Met Ile Leu Lys Lys Glu Leu Glu Ser
        195                 200                 205

Arg Gly Val Lys Phe Arg Glu Leu Ile Asn Ser Ile Arg Ile Ser Tyr
    210                 215                 220

Ser Ile Ser Leu Met Lys Thr Gly Glu Phe Lys Ile Lys Gln Ile Ala
225                 230                 235                 240

Tyr Gln Ser Gly Phe Ala Ser Val Ser Tyr Phe Ser Thr Val Phe Lys
                245                 250                 255

Ser Thr Met Asn Val Ala Pro Ser Glu Tyr Leu Phe Met Leu Thr Gly
            260                 265                 270

Val Ala Glu Lys
        275


<210> SEQ ID NO 7
<211> LENGTH: 276
<212> TYPE: PRT
<213> ORGANISM: Vibrio cholerae

<400> SEQUENCE: 7

Met Ile Gly Lys Lys Ser Phe Gln Thr Asn Val Tyr Arg Met Ser Lys
1               5                   10                  15

Phe Asp Thr Tyr Ile Phe Asn Asn Leu Tyr Ile Asn Asp Tyr Lys Met
            20                  25                  30

Phe Trp Ile Asp Ser Gly Ile Ala Lys Leu Ile Asp Lys Asn Cys Leu
        35                  40                  45

Val Ser Tyr Glu Ile Asn Ser Ser Ser Ile Ile Leu Leu Lys Lys Asn
    50                  55                  60

Ser Ile Gln Arg Phe Ser Leu Thr Ser Leu Ser Asp Glu Asn Ile Asn
65                  70                  75                  80

Val Ser Val Ile Thr Ile Ser Asp Ser Phe Ile Arg Ser Leu Lys Ser
                85                  90                  95

Tyr Ile Leu Gly Asp Leu Met Ile Arg Asn Leu Tyr Ser Glu Asn Lys
            100                 105                 110

Asp Leu Leu Leu Trp Asn Cys Glu His Asn Asp Ile Ala Val Leu Ser
        115                 120                 125

Glu Val Val Asn Gly Phe Arg Glu Ile Asn Phe Ser Asp Glu Phe Leu
    130                 135                 140

Lys Val Phe Phe Ser Gly Phe Phe Ser Lys Val Glu Lys Lys Tyr Asn
145                 150                 155                 160

Ser Ile Phe Ile Thr Asp Asp Leu Asp Ala Met Glu Lys Ile Ser Cys
                165                 170                 175

Leu Val Lys Ser Asp Ile Thr Arg Asn Trp Arg Trp Ala Asp Ile Cys
            180                 185                 190

Gly Glu Leu Arg Thr Asn Arg Met Ile Leu Lys Lys Glu Leu Glu Ser
        195                 200                 205

Arg Gly Val Lys Phe Arg Glu Leu Ile Asn Ser Ile Arg Ile Ser Tyr
    210                 215                 220

Ser Ile Ser Leu Met Lys Thr Gly Glu Phe Lys Ile Lys Gln Ile Ala
225                 230                 235                 240

Tyr Gln Ser Gly Phe Ala Ser Val Ser Tyr Phe Ser Thr Val Phe Lys
                245                 250                 255

Ser Thr Met Asn Val Ala Pro Ser Glu Tyr Leu Phe Met Leu Thr Gly
            260                 265                 270

Val Ala Glu Lys
        275
```

-continued

<210> SEQ ID NO 8
<211> LENGTH: 27
<212> TYPE: DNA
<213> ORGANISM: Artificial Sequence
<220> FEATURE:
<223> OTHER INFORMATION: pUC18-ori-MluIF primer

<400> SEQUENCE: 8
ccgcgcacgc gtatgtgagc aaaaggc 27

<210> SEQ ID NO 9
<211> LENGTH: 27
<212> TYPE: DNA
<213> ORGANISM: Artificial Sequence
<220> FEATURE:
<223> OTHER INFORMATION: pUC18-ori-KpnIR primer

<400> SEQUENCE: 9
cgcgccggta cccccgtaga aaagatc 27

<210> SEQ ID NO 10
<211> LENGTH: 27
<212> TYPE: DNA
<213> ORGANISM: Artificial Sequence
<220> FEATURE:
<223> OTHER INFORMATION: zot-MluIF primer

<400> SEQUENCE: 10
cgcgcgacgc gtttctcttt atcgatg 27

<210> SEQ ID NO 11
<211> LENGTH: 27
<212> TYPE: DNA
<213> ORGANISM: Artificial Sequence
<220> FEATURE:
<223> OTHER INFORMATION: 3'UTR-KpnIR primer

<400> SEQUENCE: 11
ccggccggta cccaagactc gctagcg 27

<210> SEQ ID NO 12
<211> LENGTH: 30
<212> TYPE: DNA
<213> ORGANISM: Artificial Sequence
<220> FEATURE:
<223> OTHER INFORMATION: MluI primer

<400> SEQUENCE: 12
ccggcgacgc gtcctttctc gcccagtgcc 30

<210> SEQ ID NO 13
<211> LENGTH: 30
<212> TYPE: DNA
<213> ORGANISM: Artificial Sequence
<220> FEATURE:
<223> OTHER INFORMATION: 5'UTR MluIF primer

<400> SEQUENCE: 13
cgcccgacgc gttagagaca aaatgttcct 30

<210> SEQ ID NO 14
<211> LENGTH: 27
<212> TYPE: DNA
<213> ORGANISM: Artificial Sequence
<220> FEATURE:

-continued

```
<223> OTHER INFORMATION: 5'-119MluIF primer

<400> SEQUENCE: 14

cgcccgacgc gtgcctgtcc gctgtgg                                    27


<210> SEQ ID NO 15
<211> LENGTH: 30
<212> TYPE: DNA
<213> ORGANISM: Artificial Sequence
<220> FEATURE:
<223> OTHER INFORMATION: B33Ch2MluF primer

<400> SEQUENCE: 15

cgcccgacgc gtatgatgtt tttattccac                                 30


<210> SEQ ID NO 16
<211> LENGTH: 32
<212> TYPE: DNA
<213> ORGANISM: Artificial Sequence
<220> FEATURE:
<223> OTHER INFORMATION: toxT-XbaIF primer

<400> SEQUENCE: 16

ccggcctcta gatacgtgga tggctctctg cg                              32


<210> SEQ ID NO 17
<211> LENGTH: 30
<212> TYPE: DNA
<213> ORGANISM: Artificial Sequence
<220> FEATURE:
<223> OTHER INFORMATION: toxTSacIR primer

<400> SEQUENCE: 17

ccggccgagc tccacttggt gctacattca                                 30
```

PLASMID-BASED CTX PHAGE REPLICATION SYSTEM AND VIBRIO CHOLERAE STRAIN THAT CAN BE INFECTED BY CTX PHAGE AND CAN BE USED FOR CHOLERA TOXIN PRODUCTION

CROSS-REFERENCE TO RELATED APPLICATIONS

This application is a Continuation of International Application No. PCT/KR2017/014782 filed Dec. 15, 2017, which claims benefit of priority to Korean Patent Application No. 10-2016-0172681 filed Dec. 16, 2016, Korean Patent Application No. 10-2016-0172684 filed Dec. 16, 2016, and Korean Patent Application No. 10-2017-0144851 filed Nov. 1, 2017, the entire content of which is incorporated herein by reference.

REFERENCE TO AN ELECTRONIC SEQUENCE LISTING

The contents of the electronic sequence listing (sequencelisting.txt; Size: 12,789 bytes; and Date of Creation: Jun. 14, 2019) is herein incorporated by reference in its entirety.

BACKGROUND

1. Field of the Invention

The present invention relates to a plasmid-based CTX phage replication system and *Vibrio cholerae* strain that can be infected by CTX phage and can be used for cholera toxin production.

2. Discussion of Related Art

Toxigenic *Vibrio cholerae* (*V. cholerae*) is generated by inserting a lysogenized CTX phage having a toxin gene into the chromosome of *V. cholerae*. Serotype O1 and O139 strains, which can be classified into three biotypes such as classical, El Tor and atypical El Tor, produce toxins, and thus epidemic cholera is developed. Classical biotype strains have the CTX-cla phage, prototype El Tor strains have CTX-1, and atypical El Tor strains are Wave 2 strains harboring CTX-2 and Wave 3 strains harboring CTX-3 to CTX-6. The O139 serotype strains have CTX-1 or CTX-O139. Toxigenic strains are generated through infection by a CTX phage, which is a virus having the cholera toxin gene, and subsequent lysogenization thereof. While a model for an evolutionary mechanism through which a strain producing a toxin is generated by infection by each biotype strain has been suggested, the infection and replication of the CTX phage are not limited by biotypes of a host strain. Recently, atypical El Tor strains having CTX phages appearing to be formed by mosaics of CTX-cla and CTX-1 have become mainstream worldwide.

The evidence that replication of CTX-1 and CTX-O139 phages is possible under laboratory conditions and the evidence of mechanisms for generating Wave 2, 3 atypical El Tor strains suggest that replication of a CTX-cla phage and a similar phage CTX-2 occurs in nature, but is not proved experimentally.

Meanwhile, conventional CTX phage replication was performed using El Tor biotype *V. cholerae*, in which the CTX phage had been previously lysogenized (Brigid M Davis et al. *Current Opinion in Microbiology,* 2003, 6: 35-42), and it has been known that $CTX^{El\ Tor}$ (CTX-1) can be made into a replicative form in a prophage state and can also be transduced. However, a CTX-CTX repeat or CTX-RS1 array is needed, and at this time, the replicated CTX-1 has been known to be only transduced in a classical biotype strain. The replicative form of CTX-1 has a plasmid-like form (pCTX-1), and the replicative form of CTX-1 transduced into a classical biotype strain may replicate a CTX phage and transduce a different classical strain with the CTX phage.

On the other hand, it has been known that $CTX^{cla}$ has no CTX-CTX array, and does not replicate because of no transducible El Tor strain, and replication of $CTX^{cla}$ and CTX-2 under laboratory conditions has not been proven.

SUMMARY OF THE INVENTION

The present invention is directed to providing a recombinant plasmid for replicating a CTX phage which includes the genomic sequence of a *Vibrio cholera* CTX phage and is replicable in host cells.

The present invention is also directed to providing a host cell transformed by the plasmid.

The present invention is also directed to providing a method of producing a *Vibrio cholerae* CTX phage from the host cells transformed by the plasmid.

The present invention is also directed to providing a *V. cholerae* variant strain which can be used as a recipient strain for CTX phage infection.

The present invention is also directed to providing a method of improving the infection efficiency of a CTX phage using the *V. cholerae* variant strain.

The present invention is also directed to providing a method of improving the production yield of cholera toxin using a *V. cholerae* variant strain harboring a recombinant plasmid for replicating a CTX phage or a CTX prophage.

To achieve the above-described objects, the present invention provides a recombinant plasmid for replicating a CTX phage, which includes the genomic sequence of a CTX phage in which the full-length sequence of a ctxA gene represented by SEQ ID NO: 1, and the full-length sequence of a ctxB gene represented by SEQ ID NO: 2, or fragments thereof are substituted with the base sequence of a selection marker gene.

The present invention also provides a host cell transformed by the recombinant plasmid for replicating a CTX phage.

The present invention also provides a method of preparing a CTX phage, which includes isolating and purifying a CTX phage from a culture of the host cell.

The present invention also provides a *V. cholerae* variant strain, which expresses a toxT protein in which tyrosine (Tyr) at amino acid 139 is substituted with phenylalanine (Phe) through the point mutation of a toxT gene, and the substituted toxT protein includes the amino acid sequence of SEQ ID NO: 7.

The present invention also provides a *V. cholerae* variant strain, which contains the recombinant plasmid for replicating a CTX phage and expresses the toxT protein in which Tyr at amino acid 139 is substituted with Phe through the point mutation of the toxT gene, and the substituted toxT protein includes the amino acid sequence of SEQ ID NO: 7.

The present invention also provides a *V. cholerae* variant strain, which is infected by a *V. cholerae* strain harboring one or more CTX prophages selected from the group consisting of CTX-1, CTX-cla, CTX-2, CTX-env and CTX-O139 to insert the genomic sequence of a CTX phage into its chromosome, and expresses a toxT protein in which Tyr at amino acid 139 is substituted with Phe through the point mutation of a toxT gene, and the substituted toxT protein includes the amino acid sequence of SEQ ID NO: 7.

The present invention also provides a method of preparing a *V. cholerae* variant strain, which includes inducing a UAU to UUU point mutation at the 139$^{th}$ codon of a toxT gene of a *V. cholerae* strain to express a toxT protein in which Tyr at amino acid 139 is substituted with Phe.

The present invention also provides a method of improving the infection efficiency of a CTX phage, which includes transducing the *V. cholerae* variant strain by the recombinant plasmid for replicating a CTX phage, or performing infection using a *V. cholerae* strain harboring one or more CTX prophages selected from the group consisting of CTX-1, CTX-cla, CTX-2, CTX-env and CTX-O139 as a donor strain and the *V. cholerae* variant strain as a recipient strain.

The present invention also provides a method of improving the production yield of cholera toxin, which includes single-phase culturing the *V. cholerae* variant strain under conditions of 30 to 37° C. and pH 6 to 8.

The present invention can improve the CTX phage infection efficiency for a *V. cholerae* variant strain expressing a toxT protein in which Tyr at amino acid 139 is substituted with Phe through the point mutation of a toxT gene as a recipient strain using a plasmid-based CTX phage replication system, simultaneously infect a plurality of CTX prophages, and increase the production yield of cholera toxin.

BRIEF DESCRIPTION OF THE DRAWINGS

FIG. 4A is a CTX-1kan phage produced from O395 transduced by pCTX-1kan; FIG. 4B is a CTX-2kan phage replicated from a MG116025 transductant by pCTX-2kan; and FIG. 4C is a CTX-O139kan phage produced from an O395 transductant by pCTX-O139kan (100,000×).

FIG. 6A shows the Western blot image of CtxA expression; and FIG. 6B shows the gel image of the same samples used in the Western blotting, which are stained by Coomassie Brilliant blue staining. Lanes 1 and 2 are O395, Lanes 3 and 4 are MG116025-toxT-139F, Lanes 5 and 6 are MG116025-toxT-139Y, Lanes 7 and 8 are IB4122-toxT-139Y, Lanes 9 and 10 are IB4122-toxT-139F, Lanes 11 and 12 are A213-toxT-139Y, and Lanes 13 and 14 are A213-toxT139F. The odd-numbered lanes represent samples cultured in LB media at 37° C., the even-numbered lanes represent samples cultured in LB media (pH 6.5) at 30° C., and the arrow indicates CtxA.

FIG. 7A is regarding rstR exchange between pCTX-1-kan-N1 and a tandem repeat of CTX-2 in B33, and FIG. 7B is regarding the potential of generating pCTX-2 by recombination between pCTX-1 and a tandem repeat of CTX-cla in a hypothetical classical strain.

DETAILED DESCRIPTION OF EXEMPLARY EMBODIMENTS

Figure 1:
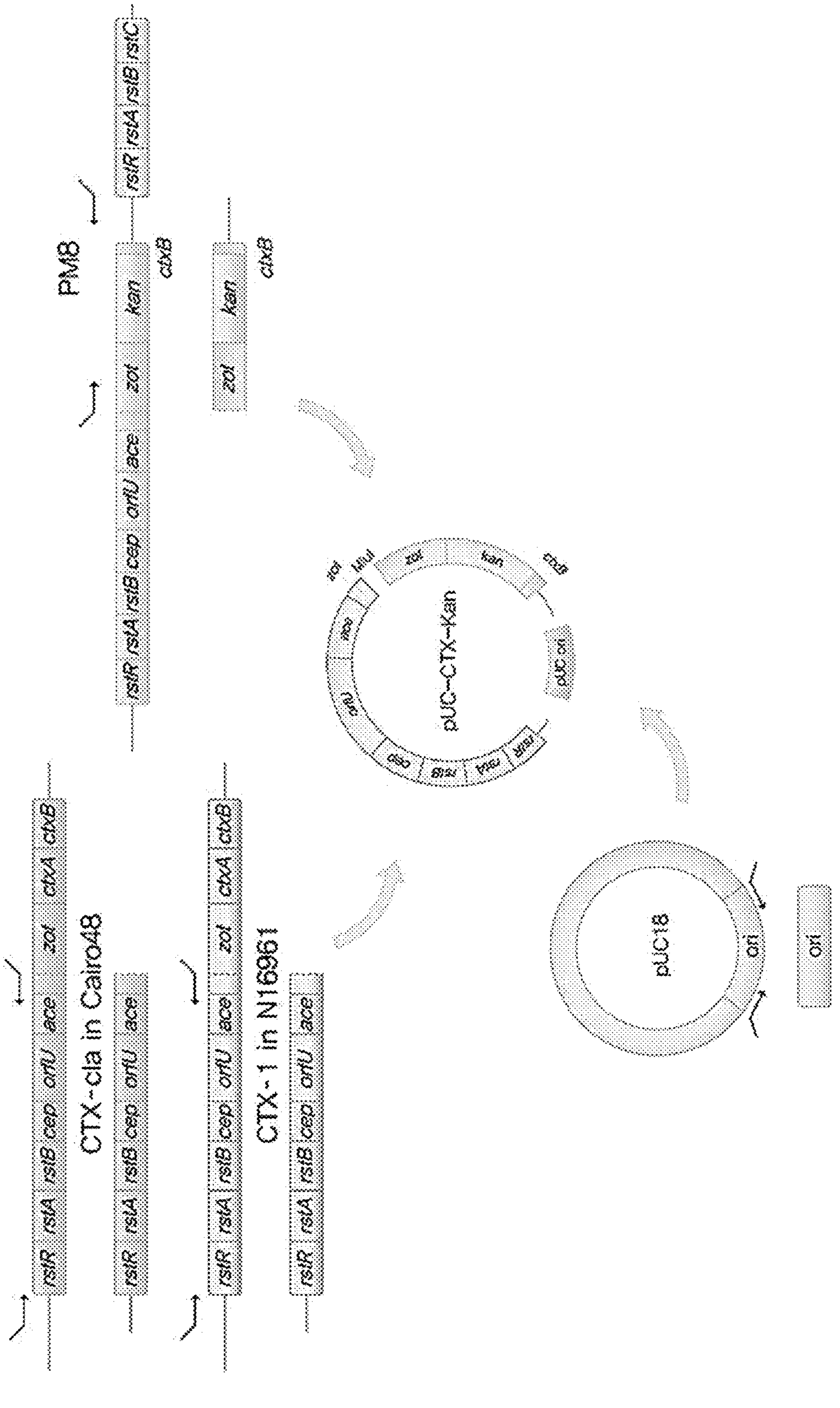
FIG. 1 illustrates the genetic map of a CTX phage and the construct of a pUC-CTX plasmid. The recombinant pUC-CTX plasmid consists of three DNA fragments, that is, a replication origin fragment of pUC18, a DNA fragment spanning from nucleotide 245 of zot to the termination codon of rstR of RS1 or CTX phage at downstream of zot amplified from PM8, and a fragment spanning the att sequence of CTX phage or from nucleotide 119 nucleotide upstream of the termination codon of rstR to nucleotide 244 of zot. Therefore, the zot-3'UTR fragment is common to all constructs, and the 5'UTR-zot fragments are phage type-specific.

Generally, CTX$^{El\ Tor}$ (CTX-1) is able to be generated from a prophage state to a replicative form and also generated by transduction. However, it has been known that a CTX-CTX repeat or CTX-RS1 array is required, and only classical biotype strains can be transduced by replicative-form CTX-1 phages. In addition, the replication of CTX$^{cla}$ (CTX-cla) has not been demonstrated under laboratory conditions because of no CTX:CTX or CTX:RS1 array and no El Tor strain to be transduced.

Therefore, the inventors constructed a plasmid-based CTX phage replication system for CTX-cla under laboratory conditions and an El Tor variant strain to be transduced by a CTX phage to demonstrate a replication process.

Accordingly, the present invention relates to a recombinant plasmid for replicating a CTX phage, which includes the genomic sequence of a CTX phage in which the full-length sequence of a ctxA gene of SEQ ID NO: 1 and the full-length sequence of a ctxB gene of SEQ ID NO: 2 or fragments thereof are substituted with the base sequences of selection marker genes.

In the present invention, a plasmid is constructed as a unit for replicating a CTX phage, amplified in *E. coli*, and then injected into *V. cholerae* to be replicated. The CTX phage generated from the plasmid is the same as a phage generated in nature. The genome of the CTX phage injected into a plasmid is capable of being artificially synthesized. Since the CTX replication can occur in a plasmid, both $CTX^{El\ Tor}$ and $CTX^{cla}$ can be produced. This suggests that different CTX phages (CTX-2, CTX-O139 and CTX-env) may be produced. As the El Tor strain capable of being transduced by $CTX^{cla}$ was newly found, it can be confirmed that $CTX^{cla}$ can be transduced.

El Tor strains have been previously known to be transduced by CTX-1 in a living body (specifically, in the intestine of a mouse), but were not demonstrated to be transduced under laboratory conditions. Therefore, it can be expected that, only when suitable laboratory conditions are provided, the El Tor strains may be transduced by CTX-1 as well as CTX-cla or CTX-2. Since CTX-2 having $rstR^{cla}$, as a tandem repeat, was contained on chromosome 2 of a Wave 2 atypical El Tor strain, CTX-2 replication can be expected, but had not been experimentally demonstrated. It can also be considered that this is because there was no El Tor strain transduced by CTX-2 or CTX-cla.

The recombinant plasmid for replicating a CTX phage of the present invention will be described in detail as follows.

The recombinant plasmid for replicating a CTX phage includes the genomic sequence of a CTX phage in which the full-length sequence of a ctxA gene and the full-length sequence of a ctxB gene or fragments thereof are substituted with a selection marker gene.

The genomic sequence of the CTX phage may be one or more genomic sequences of CTX-1, CTX-cla, CTX-2, CTX-env and CTX-O139.

In one exemplary embodiment of the present invention, the genome of the CTX-1 phage consists of rstR, rstA, rstB, cep, orfU, ace, zot, ctxA and ctxB genes.

In the recombinant plasmid for replicating a CTX phage of the present invention, the full-length sequence of the ctxA gene and the full-length sequence of the ctxB gene or fragments thereof may be substituted with a selection marker gene cassette.

The full-length sequence of the ctxA gene may be the base sequences of SEQ ID NO. 1. In addition, the full-length sequence of the ctxB gene may be the base sequences of SEQ ID NO: 2. The fragment of the ctxB gene may include the base sequences of SEQ ID NO: 3.

In addition, a selection marker gene such as a drug-resistance gene facilitates the detection of a transductant due to a phenotype of the selection marker gene in the transductant. As the selection marker gene, an ampicillin-resistance gene, a kanamycin-resistance gene, a streptomycin-resistance gene, a tetracycline-resistance gene, an erythromycin-resistance gene or a chloramphenicol acetyl transferase gene may be used. More specifically, in the present invention, the kanamycin-resistance gene may be substituted for the full-length sequence of the ctxA gene and the full-length sequence of the ctxB gene or fragments thereof. More specifically, the substituted kanamycin-resistance gene may include base sequences represented by SEQ ID NO: 4.

According to one embodiment of the present invention, the part in which the full-length sequence of the ctxA gene and the full-length sequence of the ctxB gene or fragments thereof are substituted with the kanamycin-resistance gene further includes 5' and 3'-non-coding sequences, and represented by sequences of SEQ ID NO: 5.

The recombinant plasmid for replicating a CTX phage of the present invention may contain a region essential for self-replication of the plasmid (a replication regulatory region, or a gene expression cassette). Even when a region other than the replication regulatory sequence, that is, a region excluding a replication origin and a region including genes necessary for replication, is deleted, the recombination plasmid may be replicated in host cells.

The replication regulatory region is a nucleic acid sequence including a promoter, and having an expression activity of regulating the expression, that is, transcription and translation, of a gene after being functionally linked to the gene subjected to expression.

The recombinant plasmid for replicating a CTX phage may be derived from a *E. coli*-derived plasmid for transformation selected from the group consisting of pUC19, pUC18, pBR322, pHSG299, pHSG298, pHSG399, pHSG398, RSF1010, pMW119, pMW118, pMW219 and pMW218.

The recombinant plasmid for replicating a CTX phage may be constructed in the same manner as known constructs such as conventional cloning vectors, expression vectors, etc.

For the preparation of plasmid DNA, the cleavage and binding of DNA and transformation, methods known by those skilled in the art may be used. The methods are disclosed in the literature [Sambrook, J., Fritsch, E. F., and Maniatis, T., "Molecular Cloning: A Laboratory Manual, Second Edition", Cold Spring Harbor Laboratory Press (1989)].

According to one embodiment of the present invention, the recombinant plasmid for replicating a CTX phage may be prepared by operably linking a selection marker gene cassette to the genomic sequence of a CTX phage from which the full-length sequence of a ctxA gene and the full-length sequence of a ctxB gene or fragments thereof are removed, and inserting the DNA fragment into the replication origin of the plasmid.

More specifically, the recombinant plasmid for replicating a CTX phage may include:

a replication origin fragment of a plasmid;

a DNA fragment including a sequence spanning nucleotide 245 of zot upstream of the genome of a CTX phage to the termination codon of rstR downstream thereof, a part of the zot gene, a selection marker gene cassette, and a partial sequence up to 3'UTR of the ctxB gene in a cholera strain having a CTX:RS1 or CTX:CTX array; and a DNA fragment including 5'UTR of a CTX phage, rstR, rstA, rstB, cep, orfU and a sequence up to nucleotide 244 of zot may be included in a cholera strain having an array with CTX at the very front. The DNA fragment may be amplified in a different type of CTX phage (CTX-1, CTX-cla, CTX-2, CTX-O139 or CTX-env) and linked to two different fragments such that different types of CTX phage genomes may be contained, respectively.

An example of the recombinant plasmid for replicating a CTX phage of the present invention is illustrated in the cleavage map of FIG. 1.

The recombinant plasmid for replicating a CTX phage of the present invention may be replicated in *E. coli*, the genus *Salmonella*, the genus *Shigella*, the genus *Klebsiella*, the genus *Pseudomonas* or the genus *Vibrio*. More specifically, the recombinant plasmid for replicating a CTX phage of the present invention may be *E. coli* or the genus *Vibrio*.

The genus *Vibrio* may include a classical biotype, an E1 Tor biotype, an atypical E1 Tor, an O139 serotype, or any serotype of *V. cholerae*. Most specifically, CTX phages can be replicated by transducing a classical biotype strain by a CTX-1 genome-cloned plasmid. A CTX-cla or CTX-2 genome-cloned plasmid can be introduced into any El Tor strain through transformation, thereby replicating a CTX-cla or CTX-2 phage, and the replicated CTX phage can be introduced into a *Vibrio cholera* strain in which a Tyr139Phe mutation is present at a toxT gene by transduction to replicate the CTX phage. Such variant strains may include an A213-toxT$^{Y139F}$ strain or an IB4122-toxT$^{Y139F}$ strain, but the present invention is not limited thereto.

Therefore, the present invention provides a host cell transformed with a recombinant plasmid for replicating a CTX phage.

A method of transforming host cells with the recombinant plasmid for replicating a CTX phage may be selected from all transformation methods known in the art without limitation, for example, selected from bacterial protoplast fusion, electroporation, and infection using a viral vector.

The host cells may be selected from *E. coli*, the genus *Salmonella*, the genus *Shigella*, the genus *Klebsiella*, the genus *Pseudomonas* or the genus *Vibrio*.

The culture of the transformed host cells may be performed in suitable media by various methods known in the art. Examples of the culture method include batch, continuous and fed-batch cultures. The fed-batch culture may include injection batch and repeated injection batch cultures, but the present invention is not limited thereto.

The medium used herein generally includes one or more of carbon sources, nitrogen sources, inorganic salts, vitamins and/or trace elements. A preferable carbon source is a saccharide such as a monosaccharide, a disaccharide or a polysaccharide. A nitrogen source is generally an organic or inorganic nitrogen compound, or a material including a compound thereof. Examples of the nitrogen sources include an ammonia gas, an ammonium salt such as ammonium sulfate, ammonium chloride, ammonium phosphate, ammonium carbonate or ammonium nitride, a nitrate, urea, an amino acid, or a complex nitrogen source, such as a corn steep liquor, soybean powder, a soy protein, a yeast extract or a meat extract. The nitrogen source may be used alone or in combination. Inorganic compounds that can be contained in media include chlorides, phosphates or sulfates of calcium, magnesium, sodium, cobalt, molybdenum, potassium, manganese, zinc, copper and iron. As a phosphorous source, phosphoric acid, potassium dihydrogen phosphate or dipotassium hydrogen phosphate, or a sodium-containing salt corresponding thereto may be used. To maintain a metal ion in a solution, a chelating agent may be added to the medium. More specifically, to enhance the replication of the CTX phage, nanomoles of mitomycin C may be added. All components in the medium are sterilized by heating (at 1.5 bar and 121° C. for 20 minutes) or sterile filtration. These components may be sterilized together or independently as needed. All components of the medium may be present at the beginning of the culture, or may be arbitrarily added by way of continuous or batch culture.

The CTX phages may be produced by isolating and purifying CTX phages from the transformed cell mass, culture or lysate of the host cells or the lysate of the culture.

Therefore, the present invention provides a method of producing CTX phages, which includes isolating and purifying CTX phages from a culture of the host cells.

In addition, the present invention relates to a *V. cholerae* variant strain, which expresses a toxT protein in which Tyr at amino acid 139 is substituted with Phe through the point mutation of a toxT gene, and the substituted toxT protein includes the amino acid sequence of SEQ ID NO: 7.

The present invention provides a method of preparing a *V. cholerae* variant strain, which includes inducing a UAU to UUU point mutation at the 139$^{th}$ codon of toxT gene of a *V. cholerae* strain to express toxT protein of SEQ ID NO: 7 in which Tyr is substituted with Phe at amino acid 139.

According to one embodiment of the present invention, the inventors found out a strain transduced by CTX-2 and CTX-cla among El Tor biotype strains. Compared with other *V. cholerae* strains, the El Tor strain has one single nucleotide polymorphism (SNP) at a toxT gene, which is a transcription activator of tcpA and ctxAB. Other El Tor strains have Tyr at amino acid 139 (SEQ ID NO: 6), whereas this strain has Phe at amino acid 139 of the toxT gene (SEQ ID NO: 7). Due to such a mutation, the strain may be transduced by a CTX phage and thus produce cholera toxin under laboratory conditions. When SNP of toxT has changed from 139Phe to the toxT allele (139Tyr) of a different El Tor strain, the stain of the present invention does not act as a transduction recipient strain. When SNP (139Phe) is introduced into toxT of other El Tor strains, these strains may be infected by CTX phages. Since toxT is directly involved in transcriptional activation of both tcp expression and ctxAB expression, when El Tor strains were cultured in a single phase, it was confirmed that toxin expression was also increased. In addition, using a plurality of recombinant plasmids for replicating a CTX phage, an E1 Tor strain having all of multiple CTX prophages can be constructed.

As a strain used to manufacture the *V. cholerae* variant strain of the present invention, a classical biotype, E1 Tor biotype, atypical E1 Tor biotype or O139 serotype *V. cholerae* strain may be used.

The *V. cholerae* variant strain may be any one of *V. cholerae* strains expressing the toxT protein of SEQ ID NO: 7 in which Tyr at amino acid 139 is substituted with Phe through the point mutation of a toxT gene without limitation, and may be, for example, a MG116025 (Matlab type III)-toxT$^{Y139F}$ strain, a B33-toxT$^{Y139F}$ strain, an A213-toxT$^{Y139F}$ strain or an IB4122-toxT$^{Y139F}$ strain, but the present invention is not limited thereto.

The *V. cholerae* variant strain of the present invention may include a CTX prophage selected from CTX-1, CTX-cla, CTX-2, CTX-env, CTX-O139 and a combination thereof.

One or more of the CTX prophages may be included by transducing a *V. cholerae* variant strain by the above-described recombinant plasmid for replicating a CTX phage selected from the group consisting of CTX-1, CTX-cla, CTX-2, CTX-env and CTX-O139; or infecting a *V. cholerae* variant strain using a *V. cholerae* strain which contains one or more CTX prophages selected from the group consisting of CTX-1, CTX-cla, CTX-2, CTX-env and CTX-O139 as a donor strain.

Accordingly, the present invention provides a *V. cholerae* variant strain, which includes the recombinant plasmid for replicating a CTX phage and expresses a toxT protein in which Tyr at amino acid 139 is substituted with Phe through the point mutation of a toxT gene, wherein the substituted toxT protein includes the amino acid sequence of SEQ ID NO: 7.

In addition, the present invention provides a *V. cholerae* variant strain, which is infected using a *V. cholerae* strain harboring one or more CTX prophages selected from the group consisting of CTX-1, CTX-cla, CTX-2, CTX-env and CTX-O139 such that the genomic sequence of the CTX phage is inserted into the chromosome of the strain, and expresses a toxT protein in which Tyr at amino acid 139 is substituted with Phe through the point mutation of a toxT gene, wherein the substituted toxT protein includes the amino acid sequence of SEQ ID NO: 7.

The "prophage" used herein may be a non-infectious type, and present in a phage state maintained in *V. cholerae* cells.

The "replicative-form CTX phage (pCTX)" is not inserted into a specific region of the *V. cholerae* chromosome and present in the form of a plasmid outside the chromosome.

The "donor strain or donor" used herein is a donor of a *V. cholerae* CTX phage, and refers to a *V. cholerae* strain in which a CTX phage is inserted into the chromosome as a lysogenic phage (lysogen), or a *V. cholerae* strain harboring a replicative-form CTX phage.

The term "recipient strain" used herein refers to a *V. cholerae* strain infected by a CTX phage produced from a donor.

The *V. cholerae* variant strain of the present invention may be increased in expression of a TcpA protein, compared with a *V. cholerae* strain expressing a wild-type toxT protein, and allows transcriptional activation of ctxAB expression, and thus the expression of cholera toxin may be increased.

The *V. cholerae* variant strain of the present invention may be used as a recipient strain for CTX phage infection to improve transduction efficiency.

Therefore, the present invention provides a method of improving the infection efficiency of a CTX phage, which includes transducing a *V. cholerae* strain with the recombinant plasmid for replicating a CTX phage of the present invention, or infecting the *V. cholerae* variant strain as a recipient strain using a *V. cholerae* strain harboring one or more CTX prophages selected from the group consisting of CTX-1, CTX-cla, CTX-2, CTX-env and CTX-O139 as a donor strain.

Generally, E1 Tor strains may not induce the production of cholera toxin under general experimental conditions. Therefore, conditions for producing the cholera toxin are induced using a method of reducing an oxygen partial pressure and increasing a $CO_2$ partial pressure under AKI conditions (biphasic culture, method of performing culture in a stationary state for 16 hours and then further culture by changing the culture condition to shaking culture), but the cholera toxin is not produced by single phase culture (condition for culturing stains only by shaking culture).

On the other hand, the *V. cholerae* variant strain of the present invention may produce the cholera toxin through single phase culture under conditions of 30 to 37° C. and pH 6 to 8.

The *V. cholerae* variant strain may be any *V. cholerae* strain expressing the toxT protein of SEQ ID NO: 7 in which Tyr at amino acid 139 is substituted with Phe through the point mutation of a toxT gene without limitation, and may be, for example, a MG116025 (Matlab type III)-toxT$^{Y139F}$ strain, B33-toxT$^{Y139F}$ strain, A213-toxT$^{Y139F}$ strain or IB4122-toxT$^{Y139F}$ strain. In addition, a classical biotype strain may also be used.

A medium that can be used according to the present invention has been described above, and will be omitted to avoid excessive duplication.

The transformed strain is single phase-cultured, and then the cholera toxin is isolated and purified from the cell mass, culture or lysate of the strain, or the lysate of the culture, thereby obtaining the cholera toxin.

Hereinafter, the present invention will be described in detail with reference to examples. However, the following examples are merely provided to illustrate the present invention, and the scope of the present invention is not limited by the following examples.

EXAMPLES

<Example 1> Construction of Plasmid-Based CTX Phage Replication System

By using a plasmid-based CTX phage replication system, the replication of various CTX phages was performed under laboratory conditions. To this end, CTX phages may be replicated from the plasmid-cloned CTX phage genome. An *E. coli*- and *V. cholerae*-compatible recombinant plasmid was constructed by linking the replication origin of pUC18, the CTX-1 phage genome in which total ctxA and a part of ctxB were substituted with a kanamycin cassette and upstream and downstream non-coding sequences of the CTX phage (FIG. 1). CTX-1 was transformed with the recombinant plasmid, and CTX phage production from the plasmid-cloned CTX phage genome was monitored through transduction of recipient strains. Cholera strains used in the experiment are listed in Table 1.

The inventors disclosed strain PM8 in an article published in 2014 (Kim, E. J., et al. (2014) Molecular insights into the evolutionary pathway of *V. cholerae* O1 atypical El Tor variants. *PLoS Pathog.* 10, e1004384), three types of host strains for the recombinant plasmid were PM14 (N16961 derivative that has lost a lysogenic CTX-1 prophage in a N16961 strain, which is a *V. cholerae* El Tor biotype strain, thus having TLC:RS1 array), O395 (classical biotype strain) and A213 (U.S. Gulf Coast strain harboring only the TLC element on chromosome 1). The transduction efficiency of CTX-1kan produced from plasmids using the host was investigated (Table 2).

To construct a CTX phage plasmid shown in FIG. 1, the 674-bp replication origin DNA fragment of pUC18 was amplified by PCR using the primer pair of pUC18-ori-MluIF (5'-CCG CGC ACG CGT ATG TGA GCA AAA GGC-3': SEQ ID NO: 8) and pUC18-ori-KpnIR (5'-CGC GCC GGT ACC CCC GTA GAA AAG ATC-3':SEQ ID NO: 9). The MluI restriction site (at nucleotide 245) of zot, which is common in various CTX phage genomes, was used for plasmid construction. A zot-3'UTR fragment extending from the nucleotide 245 of zot to the termination codon of rstR$^{El\ Tor}$ of RS1 was amplified by PCR using the primer pair of zot-MluIF (5'-CGC GCG ACG CGT TTC TCT TTA TCG ATG-3': SEQ ID NO: 10) and 3'UTR-KpnIR (5'-CCG GCC GGT ACC CAA GAC TCG CTA GCG-3': SEQ ID NO: 11) from the PM8 strain containing TLC:CTX-1kan:RS1 on chromosome 1. The fragment was common to all CTX phages constructed in the present invention. The zot genes of CTX-1 and CTX-cla are different due to 14 SNPs. However, zot does not affect the morphology of CTX phages. A recombinant plasmid consisting of the replication origin fragment of pUC18 and the zot-3'UTR fragment was first constructed, and then the 5' fragment was inserted into the MluI site of the plasmid. Two 5'UTR-zot fragments of each CTX phage were amplified using a common reverse transcription primer MluI (5'-CCG GCG ACG CGT CCT TTC TCG CCC AGT GCC-3': SEQ ID NO: 12) and a forward primer 5'UTR MluIF (from the att site, 5'-CGC CCG ACG CGT TAG AGA CAA AAT GTT CCT-3': SEQ ID NO: 13, the entire ig-1 sequence included) or 5'-119MluIF (from nucleotide-119 upstream of the termination codon of rstR of the lysogenic CTX genome, 5'-CGC CCG ACG CGT GCC TGT CCG CTG TGG-3': SEQ ID NO: 14). The 5' fragment of CTX-cla was amplified in classical strain Cairo48, and the 5' fragment of CTX-0139 was amplified in O139 strain AR1961537. Instead of 5'UTR MluIF, the 5'UTR-zot fragment of CTX-2 on chromosome 2 of strain B33 was amplified using the forward primer B33Ch2MluF (5'-CGC CCG ACG CGT ATG ATG TTT TTA TTC CAC-3': SEQ ID NO: 15).

An experiment was carried out to examine whether a CTX phage can be transferred to a recipient strain through transduction after the transformation of a *V. cholerae* strain containing no CTX prophage or a strain containing no replicative-form CTX phage with the recombinant plasmid and the replication of the CTX phage from the strain. Briefly, 0.5 mL of the supernatant of a donor strain culture grown overnight in the presence of 20 ng/mL mitomycin C was mixed with $3\times10^8$ CFU of agglutinated recipient strains (grown at 30° C., pH 6.5 in LB). The transduction efficiency of each recipient strain was calculated by the number of transductants per $6\times10^8$ CFU recipient cells per 1 mL of the supernatant of the donor strain. Since the recipient strains have different transduction efficiencies, the transduction efficiency of each recipient strain does not reflect the actual titer of the CTX phage produced from the recipient strain. The transduction efficiency was presented as the average of at least three independent experiments.

TABLE 1

Cholera strains and derivative strains thereof

| Strain name | Gene structure: CTX array in chromosome 1 | Gene structure: CTX array in chromosome 2 | Description, genome information and reference |
|---|---|---|---|
| V212-1 derivative | | | |
| V212-1 | TLC:RS1:CTX-1:RS1 | CTX-2:CTX-2 | Mutreja A, et al. (2011) Nature 477(7365): 462465 |
| PM8 | TLC:CTX-1kan:RS1 | CTX-2:CTX-2 | Kim EJ, et al. (2014) PLoSPathog10(9): e1004384 |
| PM9 | TLC:RS1:CTX-1:RS1 | CTX-2kan:CTX-2 | Kim EJ, et al. (2014) PLoS Pathog 10(9): e1004384 |
| N16961 derivative | | | Wave 1 El Tor strains |
| N16961 | TLC:CTX-1:RS1 | No element | AE003852/AE003853<br>Heidelberg JF, et al. (2000) Nature 406(6795): 477483 |
| PM20 | TLC:CTX-1-kan:RS1 | No element | Present invention |
| PM27 | TLC:RS1 | No element | Present invention |
| PM14 | TLC:RS1 | No element | Kim EJ, et al. (2014) PLoSPathog10(9): e1004384 |
| MG116025 derivative | | | Wave 2 strains (Matlab type 3) |
| MG116025 | TLC:RS1:CTX-1:RS1 | No element | ERS013135<br>Mutreja A, et al. (2011) Nature 477(7365): 462465 |
| MG116025-toxT-139Y | TLC:RS1:CTX-1:RS1 | No element | Present invention |
| PM30 | TLC:RS1:CTX-1:RS1:CTX-2-kan-N2 | No element | PM30 is a strain in which CTX-2 is inserted downstream of the second RS1 of chromosome 1 through transduction of the MG116025 strain (having the TLC:RS1:CTX-1:RS1 array in chromosome 1 and nothing in chromosome 2), and thus has the TLC:RS1:CTX-1:RS1:CTX-2-kan configuration of chromosome 1 and nothing on chromosome 2. |
| PM31 | TLC:RS1:CTX-1:RS1 | CTX-2-kan-N2 | Similar to PM30, PM31 is a strain in which CTX-2 is inserted into chromosome 2 through transduction of the MG116025 strain, and thus has the TLC:RS1:CTX-1:RS1 array in chromosome 1 and CTX-2-kan on chromosome 2. |
| PM25 | TLC:CTX-1:RS1 | No element | Present invention |
| PM32 | TLC:CTX-1:RS1:CTX-2-kan-N2 | No element | PM25 strain is a strain having TLC:CTX-1:RS1 array by removing RS1 upstream of chromosome 1 of the MG116025 strain and nothing on chromosome 2.<br>PM32 strain is a strain in which CTX-2 is inserted into chromosome 1 through transduction of the PM25 strain, and thus has the TLC:CTX-1:RS1:CTX-2-kan array on chromosome 1 and nothing on chromosome 2. |
| PM26 | TLC:RS1:RS1 | No element | Present invention |
| PM33 | TLC:RS1:RS1:CTX-1-kan-N2 | No element | PM33 is a strain in which CTX-1 is inserted downstream of RS1 of chromosome 1 through transduction of the PM26 strain, which has the TLC:RS1:RS1 array by removing CTX-1 from chromosome 1 of MG116025 and has nothing on chromosome 2, and thus has the TLC:RS1:RS1:CTX-1-kan array and nothing on chromosome 2. |
| PM28 | TLC | No element | Present invention |
| PM34 | TLC | CTX-1kan-N2 | PM34 is a strain in which CTX-1 is inserted into chromosome 2 through transduction of the PM28 strain, which has only TCL on chromosome 1 by removing both CTX-1 and RS1 from chromosome 1 of MG116025 and nothing on chromosome 2, and thus has only TLC on chromosome 1 and CTX-1-kan on chromosome 2. |

TABLE 1-continued

Cholera strains and derivative strains thereof

| Strain name | Gene structure: CTX array in chromosome 1 | Gene structure: CTX array in chromosome 2 | Description, genome information and reference |
|---|---|---|---|
| PM35 | TLC:CTX-2-kan-N2 | No element | PM35 is a strain in which CTX-2 is inserted into chromosome 1 through transduction of the PM28 strain, and thus has the TLC:CTX-2-kan array on chromosome 1 and nothing on chromosome 2. |
| PM29 | No TLC, no element | No element | Present invention |
| PM36 | CTX-2-kan-N2 | No element | PM36 is a strain in which CTX-2 is inserted into chromosome 1 through transduction of the PM29 strain, which has nothing on either chromosome 1 or 2 by removing all of TLC, RS1 and CTX-1 from MG116025, and thus has CTX-2-kan on chromosome 1 and nothing on chromosome 2. |
| O395 derivative | | | Classical biotype |
| O395 | TLC:TrunCTX-cla:CTX-cla | CTX-cla | CP000626/CP000627<br>Mutreja A, et al. (2011) Nature 477(7365): 462465 |
| PM37 | TLC:TrunCTX-cla:CTX-cla:CTX-1-kan-N2 | CTX-cla | PM37 is a strain in which CTX-1 is inserted downstream of CTX-cla of chromosome 1 in a classical biotype strain O395 (already having TLC:truncated CTX-cla:CTX-cla on chromosome 1 and CTX-cla on chromosome 2). Classical biotype strains are known to have only CTX-cla, and PM37 is a strain in which CTX-1 found only in El Tor strains is additionally inserted into a chromosome, and thus has TLC:TrunCTX-cla:CTX-cla:CTX-1-kan on chromosome 1 and CTX-cla on chromosome 2. |
| B33 derivative | | | Wave 2 El Tor strains |
| B33 | No TLC, no element | CTX-2:CTX-2 | ACHZ00000000<br>Faruque SM, et al. (2007) Proc Natl Acad Sci USA 104(12): 51515156 |
| PM38 | No TLC:CTX-1-kan-N2 | CTX-2:CTX-2 | PM38 is an El Tor biotype strain in which CTX-1 is inserted into chromosome 1 through transduction of the B33 strain which has nothing on chromosome 1 and the CTX-2:CTX-2 array on chromosome 2, and has CTX-1-kan on chromosome 1 and the CTX-2:CTX-2 array on chromosome 2. |
| PM21 | No TLC, no element | CTX-2 | Present invention |
| PM39 | No TLC:CTX-1-kan-N2 | CTX-2 | PM39 is a strain in which CTX-1 is inserted into chromosome 1 through transduction of PM21 strain which has only CTX-2 on chromosome 2 by removing single CTX-2 from the CTX-2:CTX-2 array having chromosome 2 of the B33 strain and nothing on chromosome 1, and thus has CTX-1-kan on chromosome 1 and CTX-2 on chromosome 2. |
| PM40 | No TLC:CTX-2-kan-N2 | CTX-2 | PM40 is a strain which has CTX-2 on each of chromosome 1 and 2 by inserting CTX-2 into chromosome 1 through transduction of PM21 strain |
| PM22 | No TLC, No element | CTX-2kan:CTX-2 | Present invention |
| IB4122 derivative | | | |
| IB4122-toxT-139Y | TLC:RS1:CTX-3 | No element | Mutreja A, et al. (2011) Nature 477(7365): 462465; Nguyen BM, et al. (2009) J Clin Microbiol 47(5): 15681571 |
| IB4122-toxT-139F | TLC:RS1:CTX-3 | No element | Present invention |
| A213 derivative | | | US Gulf Coast strain, att+; A213 derivatives are strains constructed by inserting CTX phages into chromosomes through transduction of A213. |
| A213 | TLC | No element | ERS013191; A213 derivatives are strains constructed by inserting CTX phages into the chromosomes through transduction of A213. |
| A213-toxT-139Y | TLC | No element | Mutreja A, et al. (2011) Nature 477(7365): 462465 |
| A213-toxT-139F | TLC | No element | Present invention |
| PM41 | TLC:CTX-1-kan-N1 | No element | the strain in which CTX-1 is inserted into chromosome 1 of an A213 strain |
| PM42 | TLC:CTX-1-kan-N1:CTX-1-cm-N1 | No element | the strain in which a tandem repeat of CTX-1 is inserted into chromosome 1 of an A213 strain |
| PM43 | TLC:CTX-1-kan-N2 | No element | the strain in which CTX-1 is inserted into chromosome 1 of an A213 strain |
| PM44 | TLC:CTX-1-kan-N2:CTX-1-cm-N1 | No element | the strain in which a tandem repeat of CTX-1 is inserted into chromosome 1 of an A213 strain |

TABLE 1-continued

Cholera strains and derivative strains thereof

| Strain name | Gene structure: CTX array in chromosome 1 | Gene structure: CTX array in chromosome 2 | Description, genome information and reference |
|---|---|---|---|
| PM45 | TLC | CTX-1-kan-N2 | the strain in which CTX-1 is inserted into chromosome 2 of an A213 strain |
| PM46 | TLC:CTX-1-cm-N1 | No element | the strain in which CTX-1 is inserted into chromosome 1 of an A213 strain |
| PM47 | TLC:CTX-1-cm-N1:CTX-1-kan-N1 | No element | the strain in which a tandem repeat of CTX-1 is inserted into chromosome 1 of an A213 strain |
| PM48 | TLC:CTX-1-cm-N1:CTX-1-kan-N2 | No element | the strain in which a tandem repeat of CTX-1 is inserted into chromosome 1 of an A213 strain |
| PM49 | TLC:CTX-1-cm-N1:CTX-1-kan-N2 | CTX-1-kan-N2 | PM49 is a strain in which CTX-1 is further inserted into chromosome 2 through transduction of the PM48 strain, and thus has the TLC:CTX-1:CTX-1 array on chromosome 1 and CTX-1 on chromosome 2. |
| PM50 | TLC:CTX-1-cm-N1 | CTX-1-kan-N2 | PM50 is a strain which has TC1:CTX-1 on chromosome 1 and CTX-1 on chromosome 2 by inserting CTX-1 into each of chromosome 1 or 2 of A213strain. |
| PM51 | TLC:CTX-1-cm-N1 | CTX-2-kan-N2 | the strain in which CTX-1 is inserted into chromosome 1 and CTX-2 is inserted into chromosome 2 in A213 |
| PM52 | TLC:CTX-2-kan-N2 | No element | the strain in which CTX-2 is inserted into each of chromosome 1 and chromosome 2 through transduction of an A213 strain |
| PM53 | TLC | CTX-2-kan-N2 | the strain in which CTX-2 is inserted into each of chromosome 1 and chromosome 2 through transduction of an A213 strain |

The PM30~PM53 strains are derived from toxT-139F derivative of each parent strain.
pCTX-1-kan-N1a: constructed using a plasmid-based CTX phage replication system
pCTX-1-kan-N2b: constructed by recombination between CTX-1 and CTX-2 in V212-1
pCTX-1-cm-N1: constructed using a plasmid-based CTX phage replication system
pCTX-1-cm-N2: constructed from PM48
pCTX-2-kan-N1: constructed using a plasmid-based CTX phage replication system
pCTX-2-kan-N2: constructed from PM22, which is a B33 derivative
N1: non-coding sequence derived from pCTX-1
N2: non-coding sequence derived from pCTX-2 or pCTX-cla

TABLE 2

Transduction efficiency of selected *V. cholerae* strains and plasmid-based replication of CTX phages

| Strain name | Description | Gene structure: Chromosome 1 | Gene structure: Chromosome 2 | Generated CTX phage | Transduction recipient strain | Transduction efficiency* |
|---|---|---|---|---|---|---|
| PM20 | N16961 derivative | TLC:CTX-1kan:RS1 | No element | CTX-1kan-C1+ | O395<br>MG116025 | $1 \times 10^5$<br>$1 \times 10^2$ |
| PM14 | N16961 derivative | TLC:RS1 | No element | no | | |
| PM14-U1 | PM14 transformed with pUC-CTX-1kan | TLC:RS1 | No element | CTX-1kan-P++ | O395 | $1 \times 10^5$ |
| PM14-U2 | PM14 transformed with pUC-CTX-2kan | TLC:RS1 | No element | CTX-2kan-P | MG116025 | $2 \times 10$ |
| PM14-U3 | PM14 transformed with pUC-CTX-clakan | TLC:RS1 | No element | CTX-clakan-P | MG116025 | $1 \times 10^2$ |
| PM14-U4 | PM14 transformed with pUC-CTX-O139kan | TLC:RS1 | No element | CTX-O139kan-P | O395<br>MG116025 | $2 \times 10^2$<br>$1 \times 10$ |
| PM9 | V212-1 derivative | TLC:RS1:CTX-1:RS2 | CTX-2kan:CTX-2 | CTX-2kan-C2+ | MG116025 | $1 \times 10^3$ |
| PM22 | B33 derivative | No TLC, No element | CTX-2kan:CTX-2 | CTX-2kan-C2 | MG116025 | $5 \times 10^3$ |
| O395 | Classical strain | TLC:TrunCTX-cla:CTX-cla | CTX-cla | no | | |
| O395-U1 | O395 transformed with pUC-CTX-1kan | TLC:TrunCTX-cla:CTX-cla | CTX-cla | CTX-1kan-P | O395 | $5 \times 10^4$ |
| A213 | US Gulf Coast strain | TLC | No element | No | | |

TABLE 2-continued

Transduction efficiency of selected *V. cholerae* strains and plasmid-based replication of CTX phages

| | | Gene structure | | Generated | Transduction | Transduction |
|---|---|---|---|---|---|---|
| Strain name | Description | Chromosome 1 | Chromosome 2 | CTX phage | recipient strain | efficiency* |
| A213-U1 | A213 transformed with pUC-CTX-1kan | TLC | No element | CTX-1kan-P | O395 | $3 \times 10^3$ |

*Transduction efficiency was calculated as the number of transductants per $6 \times 10^8$ recipient cells per 1 mL of culture supernatant of the donor strain. The data represent the average of at least three independent experiments.
$C^{+}$: denoting CTX phage produced from lysogenic phage inserted into chromosome 1 or 2
$P^{++}$: denoting CTX phage produced from phage genome cloned in recombinant plasmid As shown in Table 2, although there was a difference between host strains, when O395 was used as a recipient, ~$10^5$ transductants were obtained per 1 mL of the donor strain supernatant. This was similar to CTX-1 phage production from the lysogenic CTX-1:RS2 array of N16961. This shows that the replication and propagation of CTX phages do not depend on a host bacterial biotype. Since similar numbers of transductants were obtained from plasmids containing the entire intergenic region 1 (ig-1) sequence and the last 119 nucleotides, respectively, the 119 nucleotides upstream of rstR were sufficient to initiate CTX-1 replication in this system. Afterward, CTX phages were produced from the recombinant plasmid containing the last 119 nucleotides of ig-1.

The replication origin of pUC18 was no longer present in the transformed CTX-1kan phage genome, and the DNA sequence of CTX-1kan produced from the recombinant plasmid was identical to CTX-1kan produced from the lysogenic CTX-1kan. PM20 is the strain in which CTX-1-kan phages can be replicated from a prophage-type CTX genome, the CTX phage genome replicated from the recombinant plasmid and the CTX phage genome replicated from PM20 have the same base sequence, demonstrating that CTX phages replicated from the plasmid-cloned CTX phage genome and naturally-replicated CTX phages are the same.

<Example 2> Replication of CTX-Cla, CTX-2 and CTX-O139 in Plasmid-Based CTX Phage Replication System Based on the confirmation that CTX-1 could be replicated from a plasmid-cloned CTX phage genome in *V. cholerae*, the replication of CTX-2 and CTX-cla using the plasmid-based replication system could be predicted. Recombinant plasmids containing CTX-clakan and CTX-2kan genomes were constructed by the method described in Example 1 to transform PM14. Due to phage immunity, it was expected that classical biotype strains could not be transduced by CTX-clakan or CTX-2kan PM14, and thus it was tested whether CTX-clakan and CTX-2kan phages produced from the pUC-CTX plasmids could be used to transduce various El Tor biotype strains. Recipient El Tor strains were prepared for transduction in the same manner as the classical strains (agglutinated, that is, grown in LB (pH 6.5) at 30° C.).

TABLE 3

Replication and transduction efficiency of CTX-cla or CTX-2 from pUC-CTX-2kan or pUC-CTX-clakan

| | Primary transduction | | | | Secondary transduction | |
|---|---|---|---|---|---|---|
| Donor | pCTX produced from donor | Transduction recipient strain | Transduction efficiency | Transductant (transduction pCTX) | Transduction recipient strain | Transduction efficiency |
| PM14-U2 | pCTX-2kan-P* | MG116025 | $2 \times 10$ | MG116025 (pCTX-2kan-P) | MG116025 | $2 \times 10^4$ |
| | | | | | MG116025-toxTF139Y | 0 |
| | | | | | A213-toxTY139F | $3 \times 10^3$ |
| | | | | | IB4122 toxTY139F | 0 |
| PM14-U3 | pCTX-clakan-$P^{+}$ | MG116025-toxTF139Y | 0 | | | |
| | | MG116025 | $1 \times 10^2$ | MG116025 (pCTX-clakan-P) | MG116025 | $3 \times 10^4$ |
| | | | | | MG116025-toxTF139Y | 0 |
| | | | | | A213-toxTY139F | $2 \times 10^4$ |
| | | | | | IB4122-toxTY139F | 0 |
| PM9 | pCTX-2kan-$VL^{++}$ | MG116025-toxTF139Y | 0 | | | |
| | | MG116025 | $1 \times 10^3$ | MG116025 (pCTX-2kan-VL) | MG116025 | $2 \times 10^7$ |
| | | | | | MG116025-toxTF139Y | 0 |
| | | | | | A213-toxTY139F | $1 \times 10^6$ |

TABLE 3-continued

Replication and transduction efficiency of CTX-cla or CTX-2 from pUC-CTX-2kan or pUC-CTX-clakan

| | Primary transduction | | | | Secondary transduction | |
|---|---|---|---|---|---|---|
| Donor | pCTX produced from donor | Transduction recipient strain | Transduction efficiency | Transductant (transduction pCTX) | Transduction recipient strain | Transduction efficiency |
| | | | | | IB4122-toxTY139F | $1 \times 10^3$ |
| | | MG116025-toxTF139Y | 0 | | | |

*pCTX-2kan-P: pCTX-2kan is produced from plasmid pUC-CTX-2kan.
+pCTX-clakan-P: pCTX-clakan is produced from plasmidpUC-CTX-clakan.
++pCTX-2kan-VL: pCTX-2kan is produced from lysogenic CTX-2 in PM9, which is a derivative of a V212-1 strain.
MG116025-toxTF139Y: MG116025 strain in which F at amino acid 139 is substituted with Y through the point mutation of the toxT gene As shown in Table 3, no El Tor strains were transduced by CTX-clakan and CTX-2kan except Wave 2 El Tor strain MG116025. This strain was transduced by CTX-clakan and CTX-2kan phages replicated using the plasmid-based replication system. Approximately 100 and 20 transductants were obtained from the plasmid-cloned CTX-clakan and CTX-2kan genomes, respectively. The replication of CTX-clakan and CTX-2kan was confirmed by secondary transduction. Based on these results, the replication of CTX-2 and CTX-cla was confirmed with a suitable recipient strain, demonstrating the proper operation of the plasmid-based CTX phage replication system. Similarly, CTX-O139kan phages were also produced using the plasmid-based replication system.

The replication of CTX-2 from a tandem repeat of lysogenic CTX-2 present on chromosome 2 of a Wave 2 El Tor (Tor 2) strain was also demonstrated. PM9 and PM22, and V212-1 and B33 were constructed as described previously. Approximately $10^3$ transductants were obtained through primary transduction of PM9 and PM22. Secondary transduction from the transductants containing replicative forms of pCTX-clakan and pCTX-2kan to CTX-cla and CTX-2 was further demonstrated. Since no classical strain containing the CTX-cla:RS1 array or the tandem repeat of CTX-cla has been reported yet, the replication of lysogenic CTX-cla in the classical biotype strains could not be proved.

<Example 3> Transduction of CTX Phage Produced from El Tor Strain N16961

To identify genetic changes facilitating the susceptibility of the MG116025 strain to a CTX phage, genetic changes in the tcp gene cluster of MG116025, which was caused by TCP-mediated CTX phage infection, was examined.

Compared with other El Tor strains, two SNPs specific to the tcp gene cluster of MG116025 were identified from genome sequencing data. Ala56 (C269) of tcpA is changed to Asp (A269), and Tyr139 (A416) of toxT is substituted with Phe (T416) in MG116025. When Asp56 of tcpA of MG116025 is switched to Ala, the transduction efficiency was not changed or increased by up to 10 fold depending on a CTX phage, indicating that this change is not significant to the transduction-competent phenotype of MG116025. When Phe139 of toxT of MG116025 was substituted with Tyr, the transduction efficiency was decreased, suggesting that the SNPs mediate the ability of MG116025 transformed by CTX phages (Table 3-7).

Subsequently, the toxT allele (Tyr139) of two El Tor strains which were not transduced by CTX phages such as A213 and IB4122 (Wave 3 El Tor strain containing RS1: CTX-3 on chromosome 1) was substituted with the toxT allele (Phe139) of MG116025, and the ability of the strains to be transduced by CTX phages was examined.

To this end, from MG116025 and N16961 strains, a DNA fragment from 50 nucleotides upstream of the ATG initiation codon to nucleotide 793 of toxT was amplified by PCR using toxT-XbaIF (5'-CCG GCC TCT AGA TAC GTG GAT GGC TCT CTG CG-3': SEQ ID NO: 16) and toxTSacIR (5'-CCG GCC GAG CTC CAC TTG GTG CTA CAT TCA-3': SEQ ID NO: 17) primers, and inserted into suicide plasmid pCVD442. The SNP position at nucleotide 416 (A416 of N16961 and T416 of MG116025) was placed in the center of the fragment. The MG116025 toxT 139Phe allele was replaced with the toxT 139Tyr allele by an allelic exchange method, and similarly, IB4122 and A213 toxT 139Tyr alleles were replaced with the toxT 139Phe allele.

A213-toxT$^{Y139F}$ and IB4122-toxT$^{Y139F}$ were transduced by CTX phages when grown in LB (pH 6.5) at 30° C. (Tables 4 to 7), and A213 and IB4122 were not transduced by a CTX phage.

TABLE 4

Replication and production of CTX-1

| | Primary transduction | | | | Secondary transduction | |
|---|---|---|---|---|---|---|
| Donor | pCTX produced from donor | Transduction recipient strain | Transduction efficiency | Transductant (transduced pCTX) | Transduction recipient strain | Transduction efficiency |
| PM14-U1 | pCTX-1kan-P* | O395 | $1 \times 10^5$ | O395 (pCTX-1kan-P) | O395 | $5 \times 10^7$ |
| | | | | | MG116025 | $3 \times 10^5$ |
| | | | | | MG116025- | 0 |

TABLE 4-continued

| Replication and production of CTX-1 | | | | | | |
|---|---|---|---|---|---|---|
| Primary transduction | | | | | Secondary transduction | |
| Donor | pCTX produced from donor | Transduction recipient strain | Transduction efficiency | Transductant (transduced pCTX) | Transduction recipient strain | Transduction efficiency |
| | | | | | toxTF139Y | |
| | | | | | A213-toxTY139F | $1 \times 10^5$ |
| | | | | | IB4122 toxTY139F | 5 × 10 |
| PM14-U1 | pCTX-1kan-P* | MG116025 | $1 \times 10^2$ | MG116025 (pCTX-1kan-P) | O395 | $5 \times 10^6$ |
| | | | | | MG116025 | $1 \times 10^3$ |
| | | | | | MG116025-toxTF139Y | 0 |
| | | | | | A213-toxTY139F | 1 × 10 |
| | | | | | IB4122 toxTY139F | 0 |
| PM14-U1 | pCTX-1kan-P* | MG116025-toxTF139Y | 0 | | | |
| PM14-U1 | pCTX-1kan-P* | A213-toxTY139F | $1 \times 10^4$ | A213-toxTY139F (pCTX-1kan-p) | O395 | $5 \times 10^4$ |
| | | | | | MG116025 | 2 × 10 |
| | | | | | MG116025-toxTF139Y | 0 |
| | | | | | A213-toxTY139F | $2 \times 10^2$ |
| | | | | | IB4122 toxTY139F | 0 |
| PM20 | pCTX-1kan-L+ | IB4122-toxTY139F | $1 \times 10^2$ | B4122 toxTY139F (pCTX-1kan-P) | | |
| PM20 | pCTX-1kan-L+ | O395 | $1 \times 10^5$ | O395 (pCTX-1kan-L) | O395 | $3 \times 10^7$ |
| | | | | | MG116025 | $3 \times 10^5$ |
| | | | | | MG116025-toxTF139Y | 0 |
| | | | | | A213-toxTY139F | $1 \times 10^5$ |
| | | | | | IB4122 toxTY139F | $1 \times 10^3$ |
| PM20 | pCTX-1kan-L+ | MG116025 | $1 \times 10^2$ | MG116025 (pCTX-1kan-L) | O395 | $5 \times 10^4$ |
| | | | | | MG116025 | 5 × 10 |
| | | | | | MG116025-toxTF139Y | 0 |
| | | | | | A213-toxTY139F | $1 \times 10^2$ |
| | | | | | IB4122 toxTY139F | 10 |
| PM20 | pCTX-1kan-L+ | MG116025-toxTF139Y | 0 | | | |
| PM20 | pCTX-1kan-L+ | A213-toxTY139F | $1 \times 10^4$ | A213-toxTY139F (pCTX-1kan-L) | O395 | $2 \times 10^5$ |
| | | | | | MG116025 | 10 |
| | | | | | MG116025-toxTF139Y | 0 |
| | | | | | A213-toxTY139F | $1 \times 10^2$ |
| | | | | | IB4122 toxTY139F | 0 |
| PM20 | pCTX-1kan-L+ | IB4122 toxTY139F | 10 | | | |

*pCTX-1kan-P: pCTX-1kan is produced from plasmid pUC-CTX-1kan.
+pCTX-1kan-L: pCTX-1kan is produced from lysogenic CTX prophage.

TABLE 5

| Replication and production of CTX-2 | | | | | | |
|---|---|---|---|---|---|---|
| Primary transduction | | | | | Secondary transduction | |
| Donor | pCTX produced from donor | Transduction recipient strain | transduction efficiency | Transductant (transduced pCTX) | Transduction recipient strain | transduction efficiency |
| PM14-U2 | pCTX-2kan-P* | MG116025 | 2 × 10 | MG116025 (pCTX-2kan-P) | MG116025 | $2 \times 10^4$ |
| | | | | | MG116025- | 0 |

TABLE 5-continued

| Replication and production of CTX-2 | | | | | | |
|---|---|---|---|---|---|---|
| Primary transduction | | | | | Secondary transduction | |
| Donor | pCTX produced from donor | Transduction recipient strain | transduction efficiency | Transductant (transduced pCTX) | Transduction recipient strain | transduction efficiency |
| | | | | | toxTF139Y | |
| | | | | | A213-toxTY139F | 3 × $10^3$ |
| | | | | | IB4122 toxTY139F | 0 |
| | | | | | O395 | 0 |
| PM14-U2 | pCTX-2kan-P* | MG116025-toxTF139Y | 0 | | | |
| PM14-U2 | pCTX-2kan-P* | A213-toxTY139F | 10 | | | |
| PM14-U2 | pCTX-2kan-P* | IB4122 toxTY139F | 0 | | | |
| PM14-U2 | pCTX-2kan-P* | O395 | 0 | | | |
| PM22 | pCTX-2kan-BL+ | MG116025 | 5 × $10^3$ | MG116025 (pCTX-2kan-BL) | MG116025 | 1 × $10^7$ |
| | | | | | MG116025-toxTF139Y | 10 |
| | | | | | A213-toxTY139F | 4 × $10^6$ |
| | | | | | IB4122 toxTY139F | 1 × $10^2$ |
| | | | | | O395 | 300++ |
| PM22 | pCTX-2kan-BL+ | MG116025-toxTF139Y | 0 | | | |
| PM22 | pCTX-2kan-BL+ | A213-toxTY139F | 5 × $10^2$ | | | |
| PM22 | pCTX-2kan-BL+ | IB4122 toxTY139F | 10 | | | |
| PM22 | pCTX-2kan-BL+ | O395 | 0 | | | |
| PM9 | pCTX-2kan-VL+++ | MG116025 | 1 × $10^3$ | MG116025 (pCTX-2kan-VL) | MG116025 | 2 × $10^7$ |
| | | | | | MG116025-toxTF139Y | 0 |
| | | | | | A213-toxTY139F | 1 × $10^6$ |
| | | | | | IB4122 toxTY139F | 1 × $10^3$ |
| | | | | | O395 | 200++ |
| PM9 | pCTX-2kan-BL+ | MG116025-toxTF139Y | 0 | | | |
| PM9 | pCTX-2kan-BL+ | A213-toxTY139F | 1 × $10^3$ | A213-toxTY139F (pCTX-2kan-VL) | MG116025 | 2 × $10^3$ |
| | | | | | MG116025-toxTF139Y | 0 |
| | | | | | A213-toxTY139F | 2 × $10^3$ |
| | | | | | IB4122 toxTY139F | 0 |
| | | | | | O395 | 0 |
| PM9 | pCTX-2kan-BL+ | IB4122 toxTY139F | 10 | IB4122 toxTY139F (pCTX-2kan-VL) | | |

*pCTX-2kan-P: pCTX-2kan is produced from plasmid pUC-CTX-2kan.

+pCTX-2kan-BL: pCTX-2kan is produced from lysogenic CTX-2 in PM strain, which is a derivative of B33 strain.

++O395 transductants are produced by CTX-2kan (⅓ of transductants) or CTX phage (⅔ of transductants), which contains rstRE1 Tor generated by interstrand recombination between CTX-2kan and lysogenic CTX-1 in MG116025

+++pCTX-2kan-VL: pCTX-2kan is produced from lysogenic CTX-2 in PM9, which is a derivative of V212-1 strain.

TABLE 6

| Replication and production of CTX-cla | | | | | | |
|---|---|---|---|---|---|---|
| Primary transduction | | | | | | |
| Donor | pCTX produced from donor | Transduction recipient strain | transduction efficiency | Transductant (transduced pCTX) | Secondary transduction: Transduction recipient strain | Transduction efficiency |
| PM14-U3 | pCTX-clakan-P* | MG116025 | 1 × $10^2$ | MG116025 (pCTX-clakan- | MG116025 | 3 × $10^4$ |
| | | | | | MG116025- | 0 |

TABLE 6-continued

| Replication and production of CTX-cla | | | | | | |
|---|---|---|---|---|---|---|
| Primary transduction | | | | | Secondary transduction | |
| Donor | pCTX produced from donor | Transduction recipient strain | transduction efficiency | Transductant (transduced pCTX) | Transduction recipient strain | Transduction efficiency |
| | | | | P) | toxT$^{F139Y}$ | |
| | | | | | A213-toxT$^{Y139F}$ | 2 × 10$^4$ |
| | | | | | IB4122 toxT$^{Y139F}$ | 0 |
| | | | | | O395 | 0 |
| | | MG116025-toxT$^{F139Y}$ | 0 | | | |
| | | A213-toxT$^{Y139F}$ | 4 × 10 | A213-toxT$^{Y139F}$(pCTX-clakan-P) | | |
| | | IB4122 toxT$^{Y139F}$ | 3 × 10 | IB4122 toxT$^{Y139F}$ (pCTX-clakan-P) | | |
| | | O395 | 0 | | | |

*pCTX-clakan-P: pCTX-clakan is produced from plasmid pUC-CTX-clakan.

TABLE 7

| Replication and production of CTX-O139 | | | | | | |
|---|---|---|---|---|---|---|
| Primary transduction | | | | | Secondary transduction | |
| Donor | pCTX produced from donor | Transduction recipient strain | Transduction efficiency | Transductant (transduced pCTX) | Transduction recipient strain | Transduction efficiency |
| PM14-U4 | pCTX-O139kan-P* | O395 | 2 × 10$^2$ | O395 (pCTX-O139kan-P) | O395 | 1 × 10$^6$ |
| | | | | | MG116025 | 5 × 10$^3$ |
| | | | | | MG116025-toxT$^{F139Y}$ | 0 |
| | | | | | A213-toxT$^{Y139F}$ | 1 × 10$^6$ |
| | | | | | IB4122 toxT$^{Y139F}$ | 1 × 10$^2$ |
| PM14-U4 | pCTX-O139kan-P* | MG116025 | 10 | MG116025 (pCTX-O139kan-P) | O395 | 5 × 10$^6$ |
| | | | | | MG116025 | 3 × 10$^4$ |
| | | | | | MG116025-toxT$^{F139Y}$ | 0 |
| | | | | | A213-toxT$^{Y139F}$ | 3 × 10$^3$ |
| | | | | | IB4122 toxT$^{Y139F}$ | 4 × 10$^2$ |
| PM14-U4 | pCTX-O139kan-P* | MG116025-toxT$^{F139Y}$ | 0 | | | |
| PM14-U4 | pCTX-O139kan-P* | A213-toxT$^{Y139F}$ | 30 | A213-toxT$^{Y139F}$ (pCTX-O139kan-P) | | |
| PM14-U4 | pCTX-O139kan-P* | IB4122 toxT$^{Y139F}$ | 20 | IB4122 toxT$^{Y139F}$ (pCTX-O139kan-P) | | |

*pCTX-O139kan-P: pCTX-clakan is produced from plasmid pUC-CTX-O139kan.

The CTX phage infection in *V. cholerae* strains was mediated by TCP as a CTX phage recipient. Phenotypes enabling transduction of strains harboring the toxT 139Phe allele may be mediated by the high expression of TCP. TcpA expression was assessed by western blotting to monitor a TCP level.

For western blotting, bacterial strains were grown overnight in a LB medium at 30° C., subcultured in a LB medium (pH 6.5) at 30° C. or in LB diluted 1:100 at 37° C., and grown overnight again. Cells were pelleted, resuspended in 1×sample buffer, and boiled for 5 minutes. Approximately 5×10$^7$ cells were loaded onto each lane in an SDS-PAGE gel. Proteins were transferred to a Protran nitrocellulose membrane (GE Healthcare) and probed with rabbit anti-CT (Sigma) or rabbit anti-TcpA (W. F. Wade, Dartmouth University, Hanover, N.H.).

Figure 2:
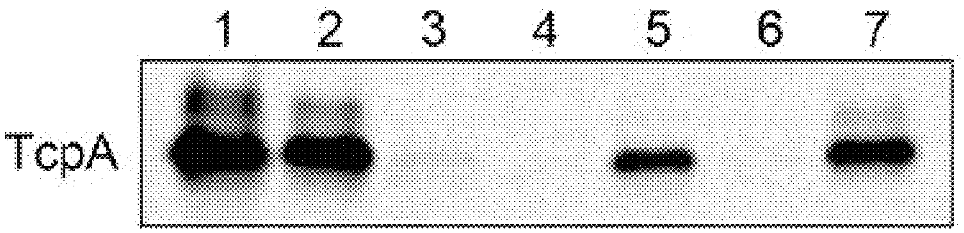
FIG. 2 shows the western blotting results comparing the expression of TcpA serving as a recipient during CTX phage infection in a strain including 139Y at toxT and a strain in which a 139F point mutation is introduced: Lane 1: O395; Lane 2: MG116025; Lane 3: MG116025-toxT$^{F139Y}$; Lane 4: IB4122; Lane 5: IB4122-toxT$^{Y139F}$; and Lane 6: A213, Lane 7: A213-toxT$^{Y139F}$.
Figure 3:
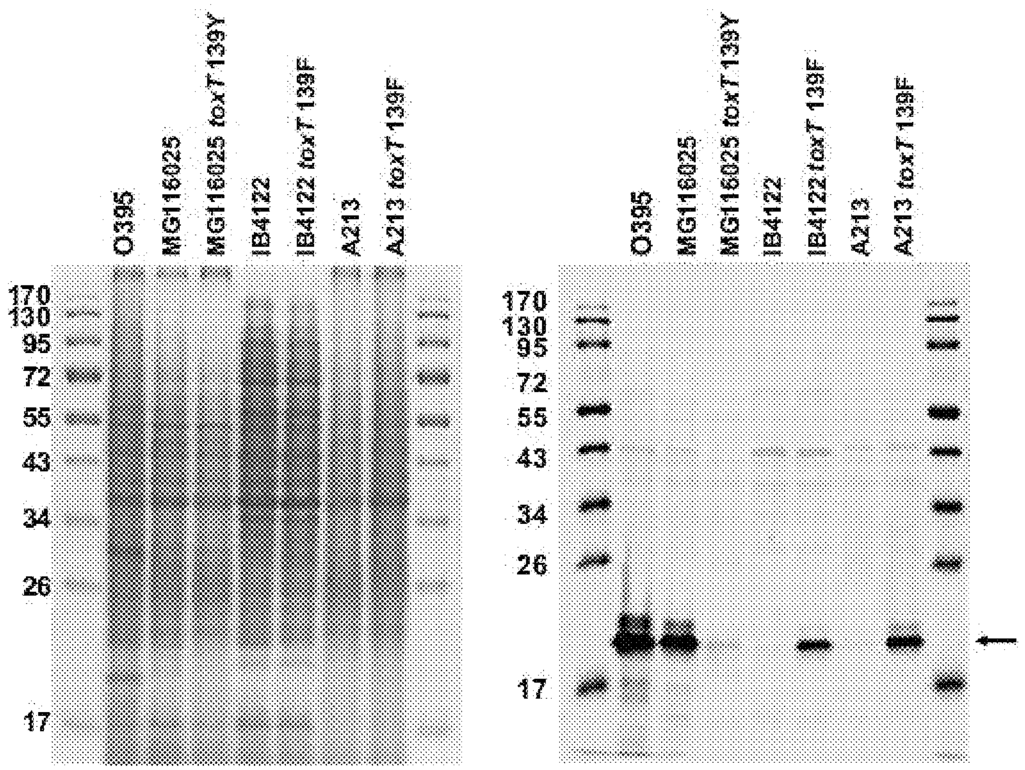
FIG. 3 shows the result of Coomassie Brilliant blue staining for determining the expression of TcpA serving as a recipient during CTX phage infection in in a strain having 139Y at toxT and a strain in which a 139F point mutation is introduced and the full-size Western blot image of the TcpA expression, wherein the arrow indicates TcpA.

As shown in FIGS. 2 and 3, while El Tor strains containing the toxT 139Phe allele expressed more TcpA, TcpA was not detected in strains containing the toxT 139Tyr allele. These results show that the toxT 139Phe allele in the El Tor strains up-regulates TCP so that CTX phage infection in bacteria may increase. Although containing the toxT133Tyr allele, high TcpA expression in the O395 strain was observed. These results have been previously known and are known as characteristics of classical biotype strains and El Tor biotype strains.

<Example 4> Replication and Transduction of CTX Phages

Figure 4A:
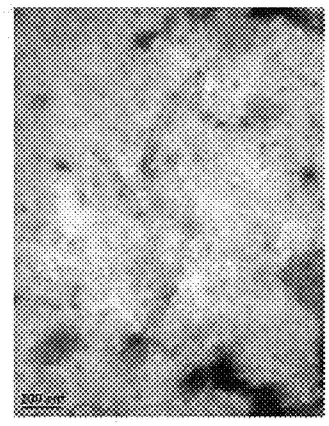
FIGS. 4A-4C show the electron microscopy images of CTX phages.
Figure 4B:
Figure 4C:
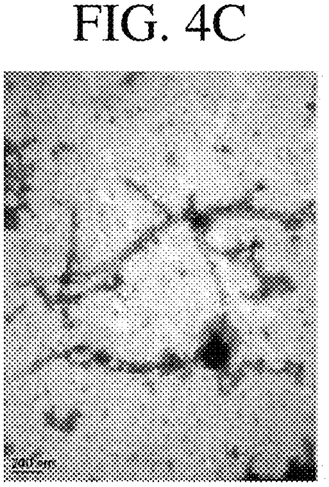

Primary and secondary transduction of various CTX phages was evaluated for O395, MG116025, A213-toxT$^{Y139F}$ and IB4122-toxT$^{Y139F}$ recipients. Briefly, El Tor strains having the toxT-Phe139 allele may be transduced by CTX phages, but efficiencies vary depending on a strain. Compared with a lysogenic or plasmid-cloned CTX phage genome (primary transduction), the production of CTX phages was ~$10^2$-fold (CTX-1 and CTX-cla) to $10^4$-fold (CTX-2 and CTX-O139) higher by replicative-form pCTXs (secondary transduction). Electron microscopy images of CTX-1kan, CTX-2kan and CTX-O139kan were obtained when the viral titer exceeded $10^6$ particles per mL (FIGS. 4A-4C). In the transductants of various CTX phages, the integration of pCTXs into chromosome 1 or 2 was confirmed.

CTX-1: When O395, A213-toxT$^{Y139F}$ and MG116025 (and IB4122-toxT$^{Y139F}$) were recipients, approximately $10^5$, $10^4$ and $10^2$ transductants were obtained from PM14-U1 (PM14 transformed with pUC-CTX-1kan) (Table 4). When O395 was a recipient, secondary transduction efficiency by pCTX-1kan in the O395 transductant increased up to 5x$10^7$, indicating that ~10% of the recipient cells were transduced by CTX-1kan. When MG116025 was a recipient, $10^4$ transductants may be obtained with the same CTX-1kan phage titer because of the phage immunity by lysogenic CTX-1 and RS1 (described below). The replication efficiency of pCTX-1kan also varied depending on a host strain. 5x$10^7$ transductants were obtained from O395 (pCTX-1kan), whereas fewer transductants (5x$10^6$ and 5x$10^4$, respectively) were produced from MG116025 (pCTX-1kan) and A213-toxT$^{Y139F}$ (pCTX-1kan). The replication efficiency of the CTX-1kan phages produced from lysogenic CTX-1 (PM20 strain) was similar to that from the pUC-CTX-1kan plasmid. Electron microscopy images of the CTX-1kan phages were obtained from the culture supernatant of O395 (pCTX-1kan) as shown in FIG. 4A.

CTX-2: pCTX-2kan replicated from a pUC-CTX-2kan plasmid was transferred to MG116025 and IB4122-toxT$^{Y139F}$ at an efficiency of 20 and 10 transductants, respectively (Table 5). Approximately 2x$10^4$ transductants were obtained in secondary transduction from the primary transductant MG116025, which harbored pCTX-2kan-P. The replication efficiency of lysogenic CTX-2 varied depending on a recipient strain. Approximately 5x$10^3$ transductants were obtained from PM22 (B33 derivative), and $10^3$ transductants were obtained from PM9 (V212-1 derivative). No CTX phage was produced from the second CTX-2 prophage of V212-1 (PM10).

A213-toxT$^{Y139F}$ was also transduced at a slightly lower efficiency than MG116025, but the transduction efficiency of IB4122-toxT$^{Y139F}$ was significantly lower. O395 classical biotype strains were also transduced by the supernatant of PM9, but pCTX transferred to O395 contained rstR$^{El\ Tor}$, which was expected to be generated by the recombination between CTX-2kan produced from the plasmid and CTX-1 on chromosome 1 and caused by the immunity imparted by rstR$^{cla}$ in lysogenic CTX-cla. Perhaps, since classical biotype strains already have the rstR$^{cla}$ gene, the efficiency of transducing CTX-2 containing rstR$^{cla}$ may be expected to be reduced.

The secondary transduction efficiency of pCTX-2kan produced from PM9 or PM22 exceeded $10^6$ when MG116025 was a recipient. A213-toxT$^{Y139F}$ and IB4122-toxT$^{Y139F}$ were transduced by a high CTX-2kan phage titer. The classical strain O395 was not transduced by a low CTX-2kan phage titer, but by a high CTX-2kan phage titer. Among several hundred transductants, approximately ⅔ of O395 transductants were transduced by a CTX phage containing rstR$^{El\ Tor}$, and ⅓ were transduced by CTX-2. Electron microscopy images of CTX-2kan phages in the culture supernatant of MG116025 (pCTX-2kan) were taken (FIG. 4B).

CTX-cla: The transduction efficiency of CTX-clakan from pUC-CTX-clakan into MG116025 was $10^2$ transductants, and $10^4$ transductants were formed in the secondary transduction (Table 6). A213-toxT$^{Y139F}$ and IB4122-toxT$^{Y139F}$ were also transduced by CTX-clakan in the primary and secondary transduction at a slightly lower efficiency than MG116025. Due to the low CTX-clakan titer, electron microscopy images of CTX-clakan phages were not obtained.

CTX-O139: The replication and production of infectious CTX-O139 from a lysogenic CTX-O139 genome were reported, and thus CTX-O139 replication from plasmid-cloned CTX-0139 was demonstrated. When O395 and MG116025 were recipients, ~200 and 10 transductants may transfer CTX-O139kan phages which were produced in PM14-U4 by transduction, respectively (Table 7). The secondary transduction efficiency increased up to $10^6$ transductants, and electron microscopy images of CTX-O139kan phages were taken (FIG. 4C). A213-toxT$^{Y139F}$ and IB4122-toxT$^{Y139F}$ were also transduced by a high CTX-O139kan phage titer.

<Example 5> Phage Immunity

To measure the degree of inhibition of superinfection of the CTX-1 phage by lysogenic CTX-1 and RS1, a set of isogenic strains of MG116025 was constructed by stepwise removal of CTX-1 and RS1 (strains PM25~PM29). To this end, MG116025, PM25 (TLC:CTX-1:RS1), PM26 (TLC:RS1:RS1), PM27 (TLC:RS1), PM28 (TLC) and PM29 (no TLC, no element) were constructed by stepwise removal of CTX-1 and RS1 on chromosome 1. pCVDrstRET which contained a DNA fragment including rstR$^{El\ Tor}$ (339 bp) and the first 226 bp of rstA was inserted independently into rstR$^{El\ Tor}$ of CTX-1 and RS1 of MG116025. The removal of CTX-1 and RS1 was verified by analyzing the genetic structure of strains selected from LB plates containing 15% (wt/vol) sucrose.

In addition, to measure phage immunity, the inhibition of CTX-1 superinfection by lysogenic CTX-1 or RS1 was monitored by measuring the transduction efficiency of isogenic strains of MG116025. MG116025 and PM25~PM29 were transfected by pCTX-1kan phages produced from O395 transductants by pCTX-1kan. The immunity against CTX-2 was tested in the same strain as the pCTX-2kan phage produced from the MG116025 transductant by pCTX-2kan.

PM28 and PM29, which do not contain CTX-1 or RS1, were transduced by CTX-1 at ~80% efficiency; when 6x$10^8$ recipient cells were used, 5x$10^8$ transductants were obtained (Table 8), which was 10-fold higher than the classical strain O395. When PM27 containing one RS1 (thus, 1 rstR$^{El\ Tor}$) was used as a recipient, transduction efficiency was almost the same. The transduction efficiency was reduced by ~$10^{-3}$-fold in PM26 and PM25 strains as well as the MG116025 strain. These results show that CTX-1 superinfection was limited by rstR$^{El\ Tor}$ of lysogenic CTX-1 or RS1. However, one rstR is not sufficient to inhibit superinfection, and at least two rstR genes are needed to inhibit the superinfection. While the superinfection of the CTX-1kan phage was restricted by the preexisting RS1 and CTX-1, the infection of rstR$^{cla}$-containing CTX-2kan was not influenced by rstR$^{El\ Tor}$ (heteroimmunity).

TABLE 8

Inhibition of superinfection of CTX-1kan phage by resident rstR$^{El\ Tor}$ in lysogenic CTX-1 and RS1

| Recipient | No. of transductants by CTX-1kan | No. of transductants by CTX-2kan |
|---|---|---|
| MG116025 (TLC:RS1:CTX-1:RS1) | 3 × $10^5$ | 5 × $10^7$ |
| PM25 (TLC:CTX-1:RS1) | 3 × $10^5$ | 4 × $10^7$ |
| PM26 (TLC:RS1:RS1) | 5 × $10^5$ | 5 × $10^7$ |
| PM27 (TLC:RS1) | 5 × $10^8$ | 6 × $10^7$ |
| PM28 (TLC) | 5 × $10^8$ | 5 × $10^7$ |
| PM29 (No TLC, No element) | 5 × $10^8$ | 5 × $10^7$ |

<Example 6> Production of toxT and Cholera Toxin

Figure 5:
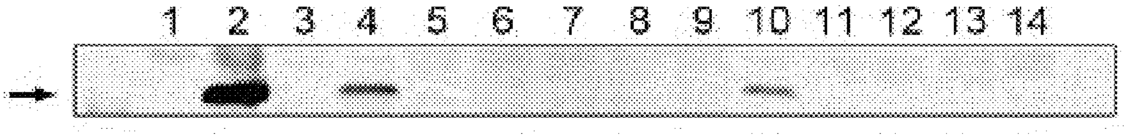
FIG. 5 shows the result of immunoblot analysis of CtxA production. Lanes 1 and 2: O395; Lanes 3 and 4: MG116025; Lanes 5 and 6: MG116025-toxT$^{F139Y}$; Lanes 7 and 8: IB4122; Lanes 9 and 10: IB4122-toxT$^{Y139F}$; Lanes 11 and 12: A213; and Lanes 13 and 14: A213-toxT$^{Y139F}$. The odd-numbered lanes represent samples grown in LB media at 37° C., the even-numbered lanes represent samples grown in LB media at pH 6.5 and 30° C., and the arrow indicates CtxA.
Figure 6A:
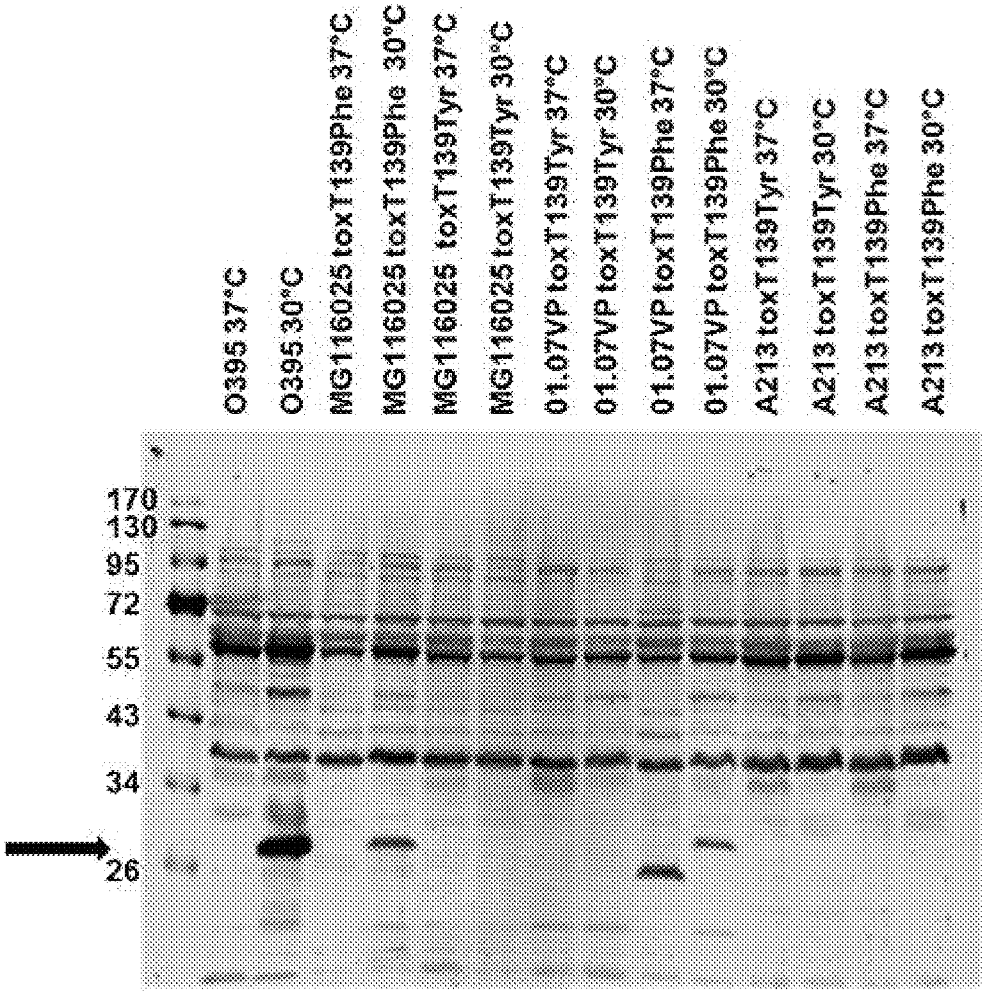
FIGS. 6A and 6B show the analysis results of CtxA expression.
Figure 6B:
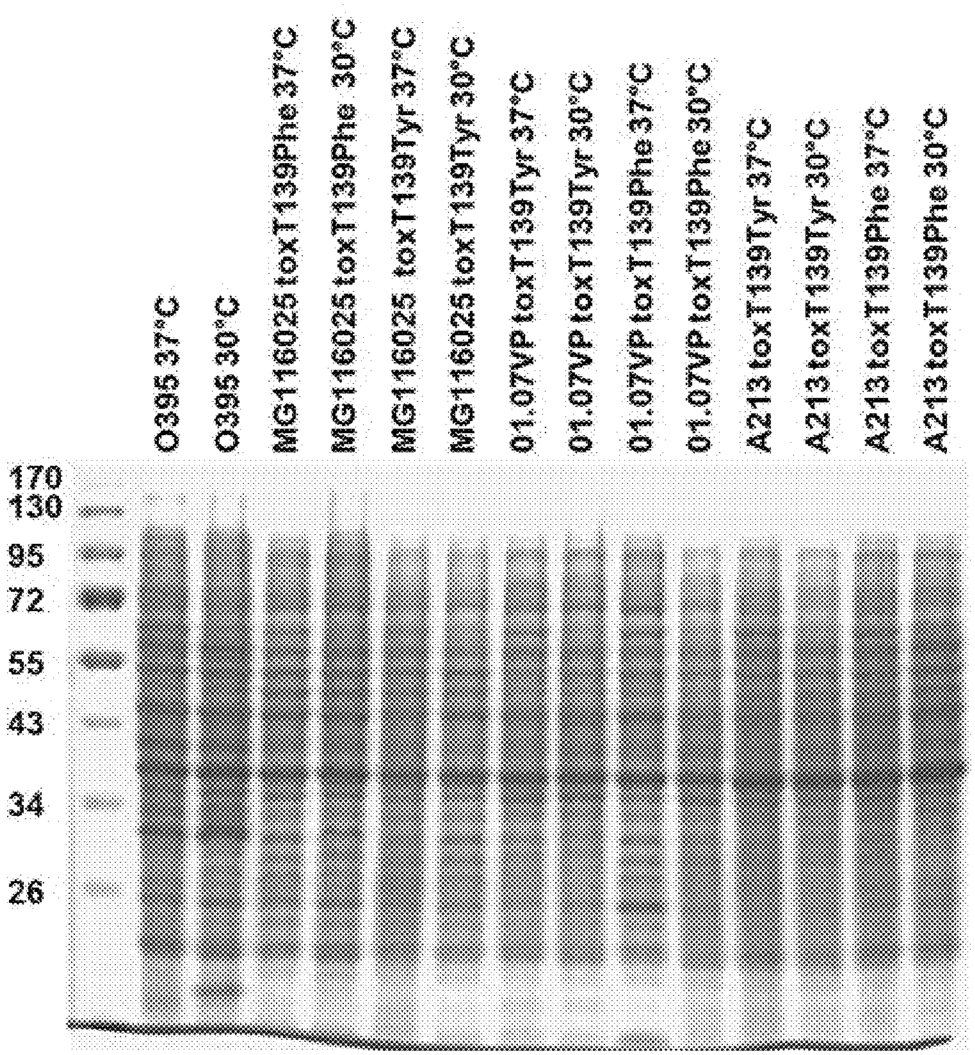

ToxT is a 32-kDa AraC family transcriptional activator. ToxT contains a conserved C-terminal DNA-binding domain including 100 amino acids, and its 176-amino acid N terminus is a dimerized domain. ToxT directly controls the expression of the tcp gene cluster and ctxAB. The toxT-F139 allele of El Tor strains up-regulated TCP at 30° C., pH 6.5, enabling the bacteria to be transduced by CTX phages. This result indicates that the toxT-F139 allele increases the expression of cholera toxin. The production of cholera toxin in *V. cholerae* strains was assessed by Western blotting (FIGS. 5-6B).

While no cholera toxin was produced in 37° C. culture, production was observed at 30° C., pH 6.5 in O395, MG116025 and IB4122-toxT$^{Y139F}$. The expression of cholera toxin was shut off in MG116025-toxT$^{F139Y}$, demonstrating that SNP in toxT mediates the increased expression of TCP and cholera toxin of El Tor biotypes under laboratory conditions.

In addition, since El Tor strains may not induce toxin production under general laboratory conditions, conditions for producing a toxin were induced using a method of lowering an oxygen partial pressure and increasing a $CO_2$ partial pressure under AKI conditions (biphasic culture, method of culturing for 16 hours in a stationary state and then culturing under different culture conditions), but no toxin was produced in single phase culture (condition for culturing a strain only in shaking culture). However, the results show that the cholera toxin can also be produced in toxT variant strains in single phase culture.

<Example 7> Construction of E1 Tor Strain Simultaneously Having Plurality of CTX Phages Since the replication and propagation methods of CTX-2 and CTX-cla, which were used in the above-describe examples, had been setup in laboratories, strains having more various CTX phages and arrays were designed and constructed. The CTX phages were transferred by transduction and inserted, and a plasmid form was removed, such that El Tor strains having both CTX-1 and CTX-2 were constructed. In addition to El Tor biotype strains, a non-typical classical strain in which CTX-1 was inserted into a classical biotype strain was also constructed. The cholera strains used in this example have been listed in Table 1.

(Construction of pCTX Phages)

pCTX-1-kan-N1 is authentic pCTX-1 having a non-coding sequence which is the same as pCTX-1, and having a kanamycin cassette which is substituted for ctxA and the first 166 bp of ctxB (Table 1). pCTX-1-kan-N1 may be generated by replication of lysogenic CTX-1-kan in a strain such as PM20, or from a plasmid-based CTX phage replication system. pCTX-1-kan-N2 may be constructed by recombination between CTX-1 and CTX-2 in a PM9 strain. pCTX-1-kan-N2 has a non-coding sequence of pCTX-2/pCTX-cla. pCTX-1-cm-N1, like CTX-1-kan-N1, may be generated using a plasmid-based CTX phage replication system. In this system, a chloramphenicol cassette is substituted instead of the kanamycin cassette. pCTX-1-cm-N2 is generated from PM48.

pCTX-cla-kan-N1 has the non-coding sequence of pCTX-1, and is generated from a plasmid-based CTX phage replication system. pCTX-2-kan-N1 is generated from a plasmid-based CTX phage replication system. pCTX-2-kan-N1 has the non-coding sequence of pCTX-1. pCTX-2-kan-N2 is generated from the CTX-2 tandem repeat of PM22 generated in B33.

The pCTX phages generated from a plasmid-based CTX phage replication system or a lysogenic CTX prophage were maintained by transduction of suitable recipient strains for maintenance, that is, transduction of an O395 classical strain using pCTX-1 or a PM27-toxT-139F strain using pCTX-2, to produce more progeny phages, and used for secondary transduction.

(Construction of MG116025 and B33 Derivative Strains)

Isogenic strains of MG116025 and PM25 to PM29 were constructed by stepwise removal of CTX-1 and RS1. PM21, which is a derivative strain of B33, contained only one CTX-2 on chromosome 2, which was similar to PM6. These strains were used to construct strains having various CTX arrays.

(Construction of CTX Phage Transduction Recipient Strains)

When cultured under agglutination conditions (LB, pH6.5, 30° C.), a pCTX-1 phage was inserted into a classical biotype strain O395. When El Tor biotype strains harbored the toxT-139F allele, the strains were transduced by CTX phages. Strains such as A213, B33, MG116025, etc. were prepared to serve as a transduction recipient by substitution with toxT-139F.

(Insertion of CTX Phages into Cholera Strains)

The CTX phages replicated in a CTX phage donor strain are transferred through transduction to a recipient strain according to a standard protocol. The insertion of pCTX into chromosome 1 or chromosome 2 and the final CTX array were confirmed by various PCR combinations. pCTX was inserted into the chromosome, and a pCTX-cured strain was screened.

<Experimental Example 1> CTX Phages and Non-Coding Sequences

The non-coding sequences (the sequence between ctxB and rstR) of pCTX-1 and pCTX-cla differ from each other. The difference in base sequence of the non-coding sequences of pCTX-1 and pCTX-cla determines the orientation of inserting CTX phages into either chromosome 1 or chromosome 2 of cholera strains. When a phage has the non-coding sequence of pCTX-1, it has been known that the sequence is inserted only into chromosome 1, and when a phage has the non-coding sequence of pCTX-cla, the sequence may be inserted into both chromosome 1 and chromosome 2. The non-coding sequences of pCTX-1 and pCTX-2 may be interchangeable. CTX-1-kan-N1 contains the non-coding sequence of authentic pCTX-1, and CTX-1-kan-N2 contains the non-coding sequence of pCTX-cla. Therefore, pCTX-1-kan-N2 can be expected to integrate into both chromosome 1 and chromosome 2, and PM34 (also PM45, 49 and 50) was indeed constructed by inserting pCTX-1-kan-N2 into chromosome 2.

The non-coding sequence of pCTX is derived from RS1 downstream of a CTX phage during the replication of CTX prophages or a different prophage. Since most El Tor strains have a CTX-1:CTX-1 array or CTX-1:RS1 array, pCTX-1 has the non-coding sequence of authentic CTX-1. However, if there are CTX-1:CTX-2 and CTX-1:CTX-cla arrays, CTX-1 having the non-coding sequence of CTX-cla may be generated while CTX-1 is replicated. Therefore, the pCTX-1-N2 phage having both the pCTX-1 genome and the non-coding sequence of CTX-cla may be present like pCTX-1-N1. When the pCTX-1-N2 phage is inserted downstream of CTX-1 of a different strain, another pCTX-1-N2 phage may be generated. In this study, pCTX-1-cm-N2 was actually generated from PM48 (Table 1).

<Experimental Example 2> Recombination Between pCTX and Prophage

Figure 7A:
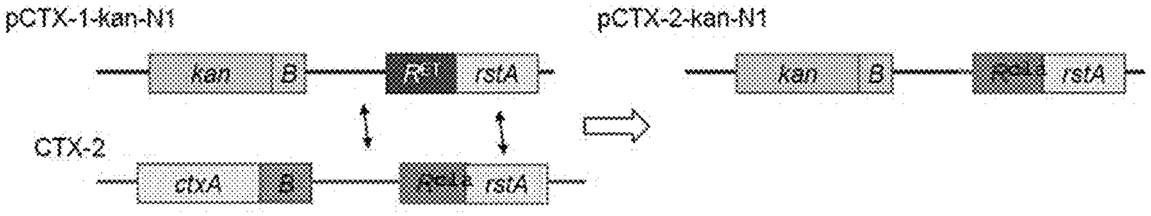
FIGS. 7A and 7B show the process of producing pCTX-2 by recombination between pCTX-1 and a tandem repeat of a CTX-2 prophage.
Figure 7B:
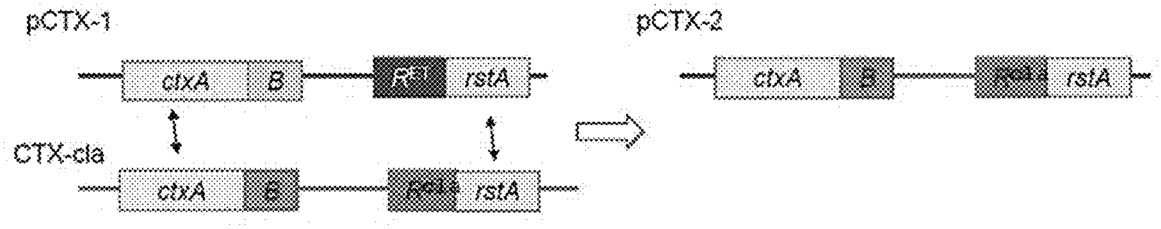

A mechanism of generating mosaic CTX phages by recombination between two different CTX phages present on different chromosomes in a single cholera strain had been previously demonstrated. Similarly, recombination between pCTX and a prophage could be possible. pCTX-1-kan-N1 is transferred to a B33-toxT-139F strain, thereby generating B33 (pCTX-1-kan-N1), and the phage progeny pCTX-1-kan-N1 generated from this strain may be transduced to O395 to avoid phage immunity. However, the recombination between pCTX-1-kan-N1 and a CTX-2 prophage may occur in B33 (pCTX-1-kan-N1), and when the recombination between rstA and a non-coding sequence, which are present at both sides of rstR of each CTX phage, occurs, pCTX-2-kan-N1 may be produced (FIG. 7A). The pCTX-2-kan-N1 produced thereby may be transferred to an El Tor strain such as MG116025. Indeed, pCTX-2-kan-N1 transferred to MG116025 through transduction was able to be identified. These results show that pCTX-2 can be generated by transducing a classical strain harboring a tandem of the CTX-cla prophage with pCTX-1 (FIG. 7B). It is also possible to have recombination between pCTX-1 and pCTX-cla.

<Experimental Example 3> Construction of Classical Biotype Strain Harboring CTX-1

Figure 8:
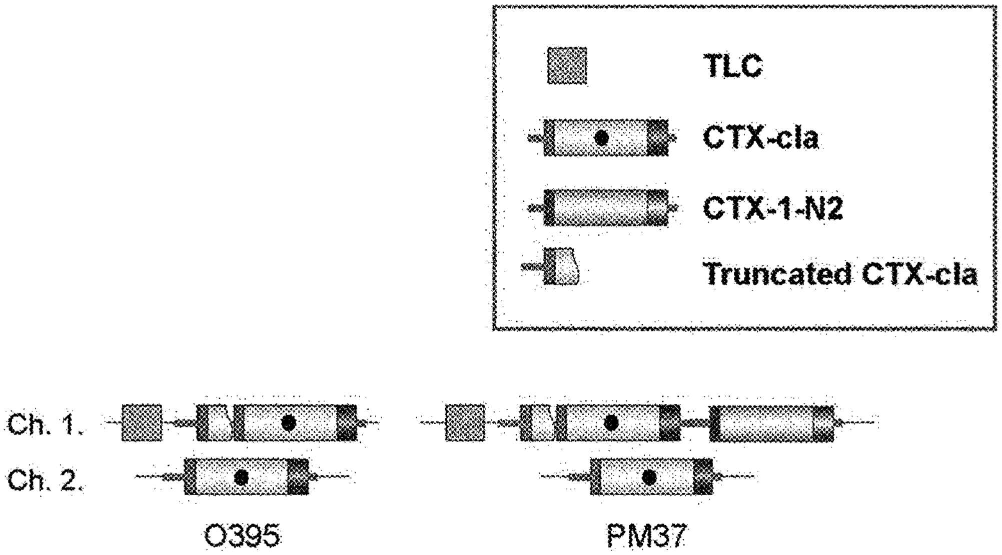
FIG. 8 shows the CTX array in classical biotype strains O395 and PM37.

While atypical El Tor strains (Wave 2) harboring CTX-2 have been found, no classical strain having CTX-1 containing $rstR^{El\ Tor}$ and $ctxB^{El\ Tor}$ has been found. Classical biotype strains are transduced by CTX-1, and while pCTX-1 is maintained in a classical biotype strain, a strain prepared by inserting CTX-1 into the chromosome of a classical biotype strain has not been found yet. As shown in FIG. 8, a strain was constructed by inserting pCTX-1-kan-N2 into chromosome 1 of O395, which is a classical biotype strain (PM37). This result shows that atypical classical strain might be present in nature.

<Experimental Example 4> Design and Construction of Various El Tor Strains

Toxigenic El Tor-type strains are generated by the integration of TLC, CTX-1 and RS1 in the dif1 base sequence of chromosome 1. In addition, it has been previously reported that strains that do not generate a toxin are generated by removing CTX-1 and RS1 from El Tor biotype strains. For example, the MG116025 strain has the TLC: RS1:CTX-1:RS1 array on chromosome 1, and a process of generating isogenic strains of the MG116025 strain, which are generated by stepwise removal of RS1, CTX-1 and even TLC (PM25~PM29), has been previously reported. In this study, various types of pCTXs are transferred to MG116025 and strains generated therefrom, El Tor strains such as B33, A213, etc., thereby constructing strains having various CTX arrays.

Figure 9:
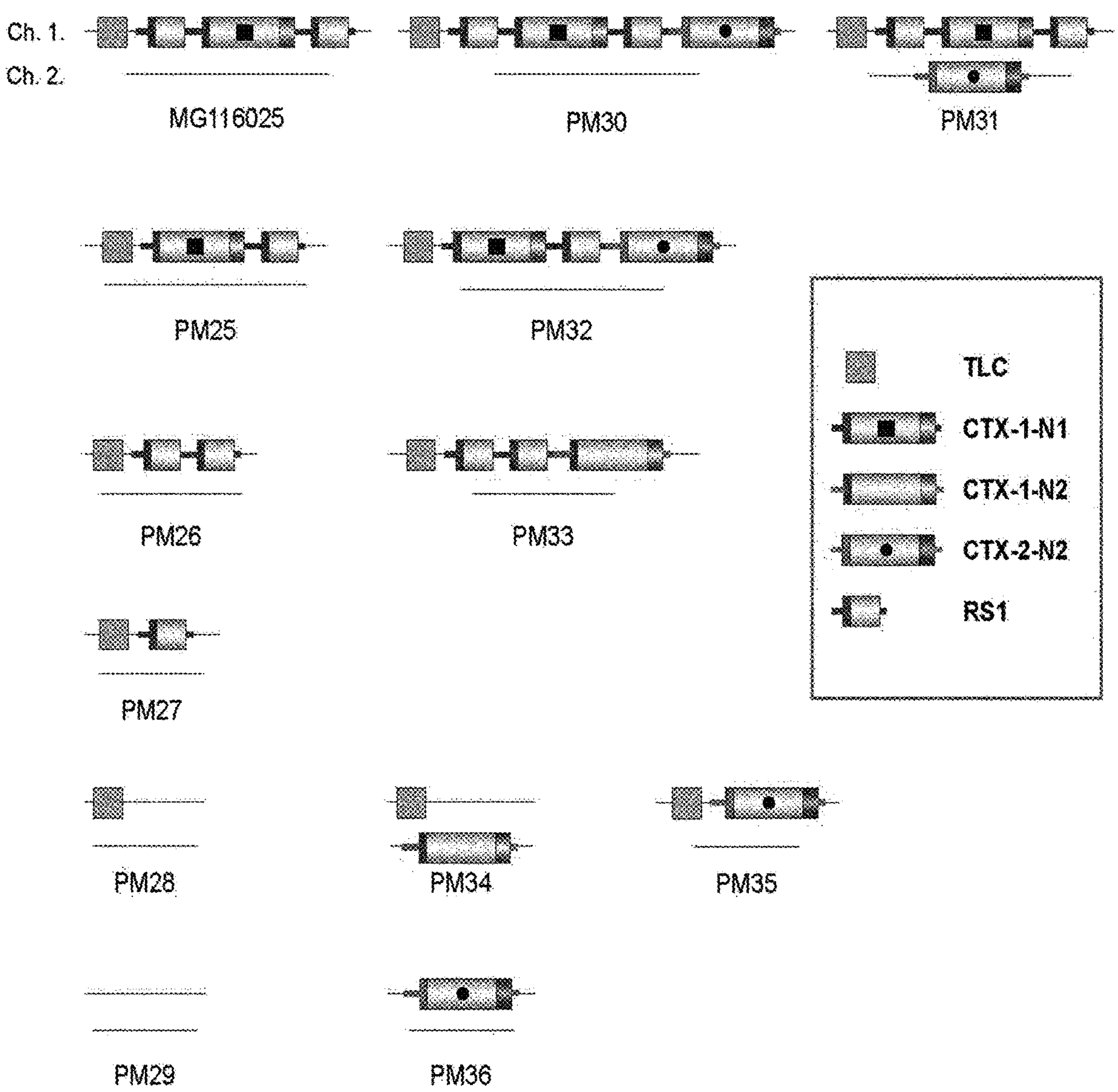
FIG. 9 shows the CTX arrays of MG116025 and derivative strains thereof: PM25~PM29 are constructed by the stepwise removal of CTX-1, RS1 and TLC from MG116025, and PM30~PM36 are constructed by the insertion of CTX-2-kan-N2 or and CTX-1-kan-N2 in parental strains.

MG116025 and derivative strains thereof: As shown in FIG. 9, MG116025 and derivative strains thereof are strains which already contain the CTX-1 phage and RS1 on their chromosomes. It was demonstrated that novel strains having various CTX arrays can be substantially designed and constructed by inserting CTX-1 and CTX-2 phages into the chromosomes of MG116025 and its derivative strains.

PM30 and PM31 strains are strains generated by inserting CTX-2 into chromosome 1 and chromosome 2 of MG116025 (FIG. 8, Table 1). Similarly, PM32 harboring TLC:CTX-1:RS1:CTX-2-kan may be generated from a PM25 strain. PM33 harboring TLC:RS1:RS1:CTX-1 on chromosome 1 may be generated by inserting pCTX-1-kan-N2 into PM26. PM28 is a strain harboring only TLC on chromosome 1, and PM34 may be generated by inserting pCTX-1-kan-N2 into chromosome 2 of PM28. In addition, PM35 is a strain generated by inserting CTX-2 into chromosome 1 of PM28. The construction of strains having more various arrays from a strain harboring only TLC will be described with strains generated from an A213 strain in further detail below. A PM36 strain was constructed by inserting CTX-2-kan-N2 into chromosome 1 of PM29, which is a strain having no TLC. These results show that it is possible to additionally introduce a CTX phage into strains conventionally harboring CTX, RS1, etc., or insert a novel CTX phage after removal of preexisting CTX and RS1.

Figure 10:
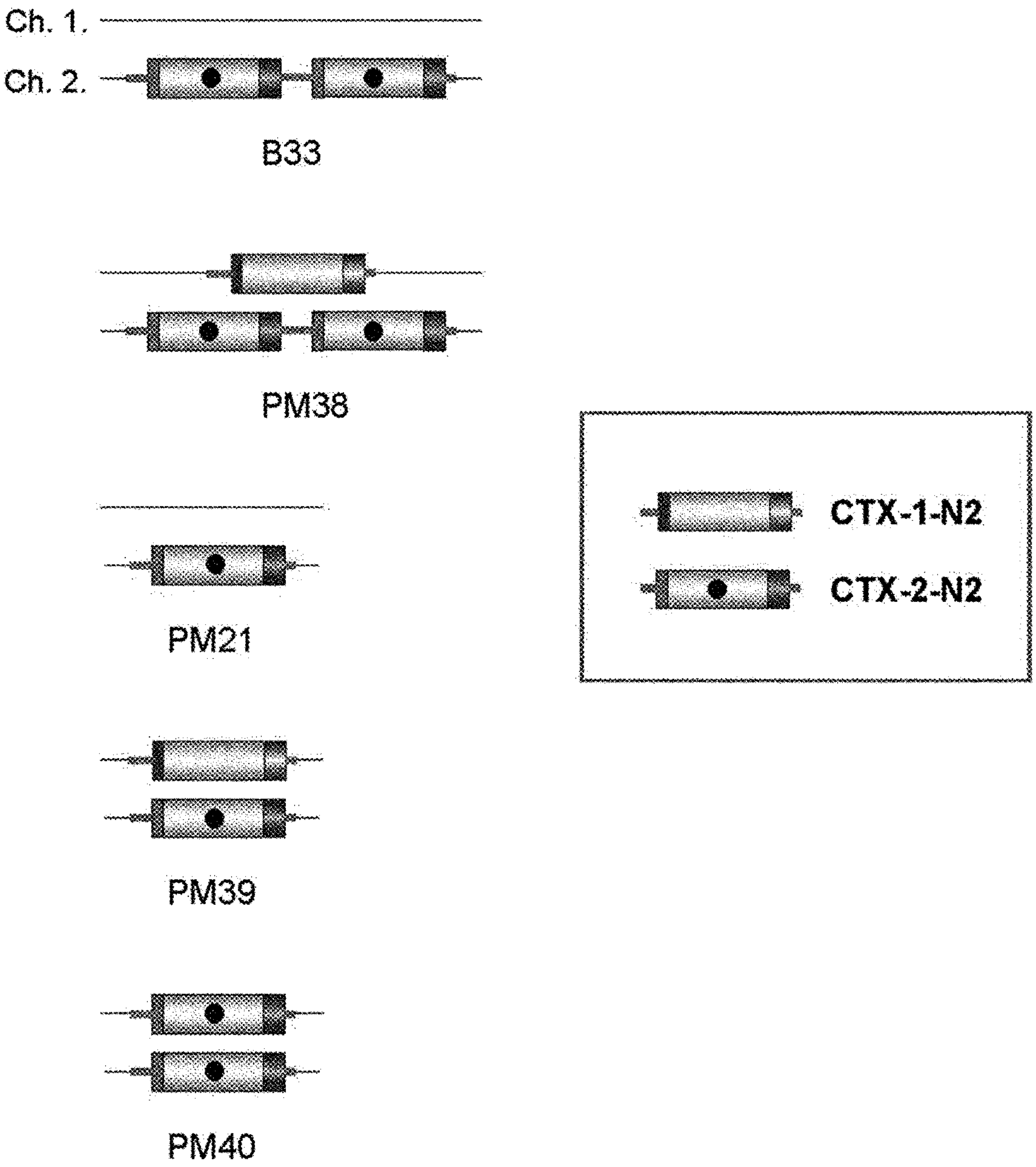
FIG. 10 shows the CTX arrays of strain B33 and derivative strains thereof: PM38 is constructed by inserting pCTX-1-kan-N2 into chromosome 1 of B33, PM21 is constructed by removing a CTX-1 prophage from chromosome 2 of B33, and PM39 and PM40 are constructed by inserting pCTX-1-kan-N2 and pCTX-2-kan-N2 into chromosome 1 of PM21, respectively.

B33 and derivative strains thereof: As shown in FIG. 10, B33 is a Wave 2 atypical El Tor strain that harbors no TLC on chromosome 1 and two tandem repeats of CTX-2 on chromosome 2. CTX-1 may be inserted into chromosome 1 of B33, thereby generating a PM38 strain, which harbors different types of CTX phages on respective chromosomes. PM21 is a strain generated by removing one CTX-2 from B33, and PM39 and PM40 may be generated by inserting CTX-1 and CTX-2 into chromosome 1 of PM21, respectively.

A213 and derivative strains thereof: A213 is a strain which is classified as a US Gulf Coast strain or a pre-seventh pandemic strain and does not harbors CTX, which might be lost during isolation or storage. This study has more focused on constructing various strains from A213, which is to demonstrate a principle for a method of constructing a strain having various CTX phage arrays since A213 is a strain harboring only TLC.

Figure 11:
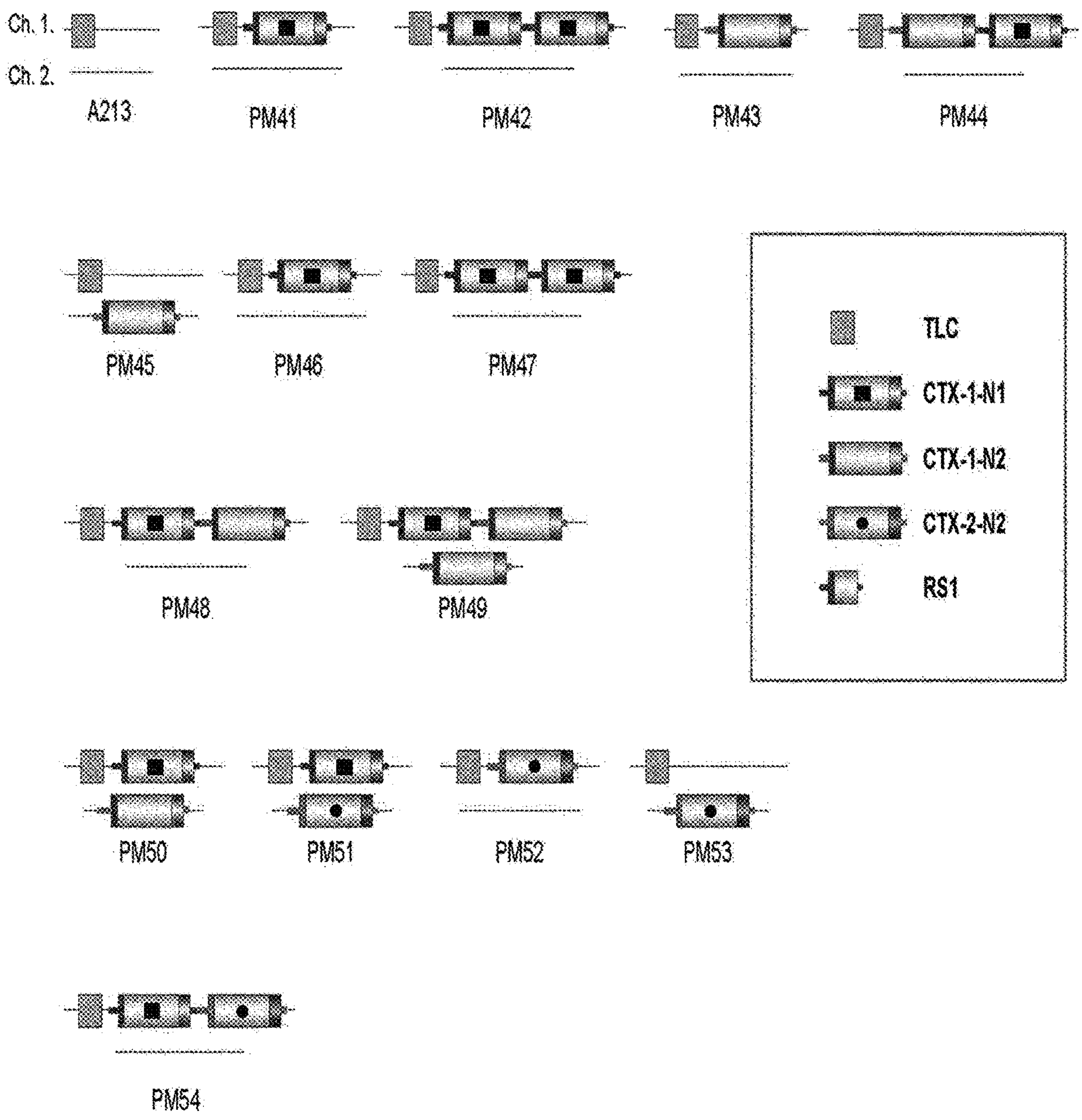
FIG. 11 shows the CTX arrays constructed from A213, and various strains constructed from non-toxic strain A213 containing only TLC to demonstrate the concept of designing and constructing strains by using various CTX arrays.

As shown in FIG. 11, a strain harboring only one CTX-1 or CTX-2 on each chromosome was constructed, and a strain harboring a tandem repeat of CTX-1 on a chromosome (PM43) was also constructed. A strain harboring CTX-1 on both chromosomes (PM50), and a strain harboring a tandem repeat of CTX-1 on chromosome 1 and CTX-1 on chromo some 2 (PM49) were also constructed. In addition, a strain harboring CTX-1 on chromosome 1 and CTX-2 on chromosome 2 (PM51) and a strain harboring solitary CTX-2 on chromosome 2 (PM53) were constructed.

The present invention can be applied in the field of producing a cholera vaccine. In addition, the present invention can be applied in order to produce cholera toxin or a toxoid.

What is claimed is:

1. A *Vibrio cholerae* variant strain, comprising:

expressing a toxT protein having the amino acid sequence of SEQ ID NO: 7 in which Tyr at amino acid 139 of SEQ ID NO: 7 is substituted with Phe through the point mutation of a toxT gene.

2. The *Vibrio cholerae* variant strain according to claim 1, wherein the *Vibrio cholerae* variant strain is used as a recipient strain for CTX phage infection.

3. The *Vibrio cholerae* variant strain according to claim 1, wherein the *Vibrio cholerae* variant strain uses a classical biotype, E1 Tor biotype, atypical E1 Tor biotype or O139 serotype *Vibrio cholerae* strain as a parental strain to prepare the *Vibrio cholerae* variant strain.

4. The *Vibrio cholerae* variant strain according to claim 1, wherein the *Vibrio cholerae* variant strain is a toxigenic *Vibrio cholerae* variant strain comprising one or more CTX prophages selected from the group consisting of CTX-1, CTX-cla, CTX-2, CTX-env, and CTX-O139 having a cholera toxin gene.

5. The *Vibrio cholerae* variant strain according to claim 1, wherein the *Vibrio cholerae* variant strain is a toxigenic *Vibrio cholerae* variant strain comprising a cholera toxin gene inserted on the chromosome of the strain.

* * * * *